United States Patent
Miller et al.

(10) Patent No.: US 11,614,438 B1
(45) Date of Patent: Mar. 28, 2023

(54) INTEGRATED GLUCOSE MONITORING SYSTEM

(71) Applicant: Tula Health, Inc., Kaysville, UT (US)

(72) Inventors: Devin Miller, Morgan, UT (US); David Miller, Morgan, UT (US); Peter Derrick, Morgan, UT (US)

(73) Assignee: Tula Health, Inc., Kaysville, UT (US)

( * ) Notice: Subject to any disclaimer, the term of this patent is extended or adjusted under 35 U.S.C. 154(b) by 409 days.

(21) Appl. No.: 16/910,741

(22) Filed: Jun. 24, 2020

(51) Int. Cl.
*G01N 33/487* (2006.01)
*A61B 5/145* (2006.01)
*A61B 5/15* (2006.01)
*A61B 5/00* (2006.01)

(52) U.S. Cl.
CPC ..... *G01N 33/48792* (2013.01); *A61B 5/0022* (2013.01); *A61B 5/1411* (2013.01); *A61B 5/14532* (2013.01); *A61B 5/742* (2013.01); *A61B 2560/0204* (2013.01); *A61B 2560/0223* (2013.01)

(58) Field of Classification Search
CPC . A61B 5/14532; A61B 5/0022; A61B 5/1411; A61B 5/742; A61B 2560/0204; A61B 2560/0223; G01N 33/48792
See application file for complete search history.

(56) References Cited

U.S. PATENT DOCUMENTS

| | | | | |
|---|---|---|---|---|
| 7,587,287 | B2* | 9/2009 | Connolly | A61B 5/14532 702/32 |
| 2003/0176183 | A1* | 9/2003 | Drucker | G01N 33/48792 455/425 |
| 2008/0045278 | A1* | 2/2008 | Kim | A61B 5/6887 455/575.1 |
| 2014/0231252 | A1* | 8/2014 | Rao | A61B 5/6898 204/403.02 |

* cited by examiner

*Primary Examiner* — Samuel P Siefke
(74) *Attorney, Agent, or Firm* — Miller IP Law, LLC

(57) ABSTRACT

An integrated glucose monitoring system comprising a glucometer and mobile device housed in a housing. The glucometer includes a measurement component to receive a blood glucose test strip containing a sample of blood of an individual, and a port to transmit the blood glucose measurement to a mobile device. The mobile device communicatively and physically coupled to the glucometer. The mobile device includes a port configured to couple with the glucometer, a communication component to receive the blood glucose measurement from glucometer, a power management component to transmit power to the glucometer, and another port to receive power from a power source to power the mobile device. The housing is to house the glucometer and the mobile device to form a single solitary glucose monitoring system.

20 Claims, 19 Drawing Sheets

INTEGRATED GLUCOSE MONITORING SYSTEM

BACKGROUND

The quality of life of an individual with a chronic health condition is greatly influenced by symptoms of the chronic health condition. The quality of life of the individual may substantially improve by proper management of a chronic health condition. For example, proper management of a chronic condition may include taking regular measurements of various body functions, either directly or indirectly. Such measurements may provide critical information necessary for proper management of the chronic health condition. Obtaining measurements may be challenging and/or time-consuming which may deter the individual from taking the measurements. Without the measurements, the chronic health condition may be improperly and/or inadequately managed, leading to poor outcomes for the individual such as serious, even life-threatening, symptoms of the chronic health condition.

BRIEF DESCRIPTION OF DRAWINGS

The present description will be understood more fully from the detailed description given below and from the accompanying drawings of various embodiments of the present embodiment, which description is not to be taken to limit the present embodiment to the specific embodiments but are for explanation and understanding. Throughout the description the drawings may be referred to as drawings, figures, and/or FIGS.

DETAILED DESCRIPTION

Figure 1A:
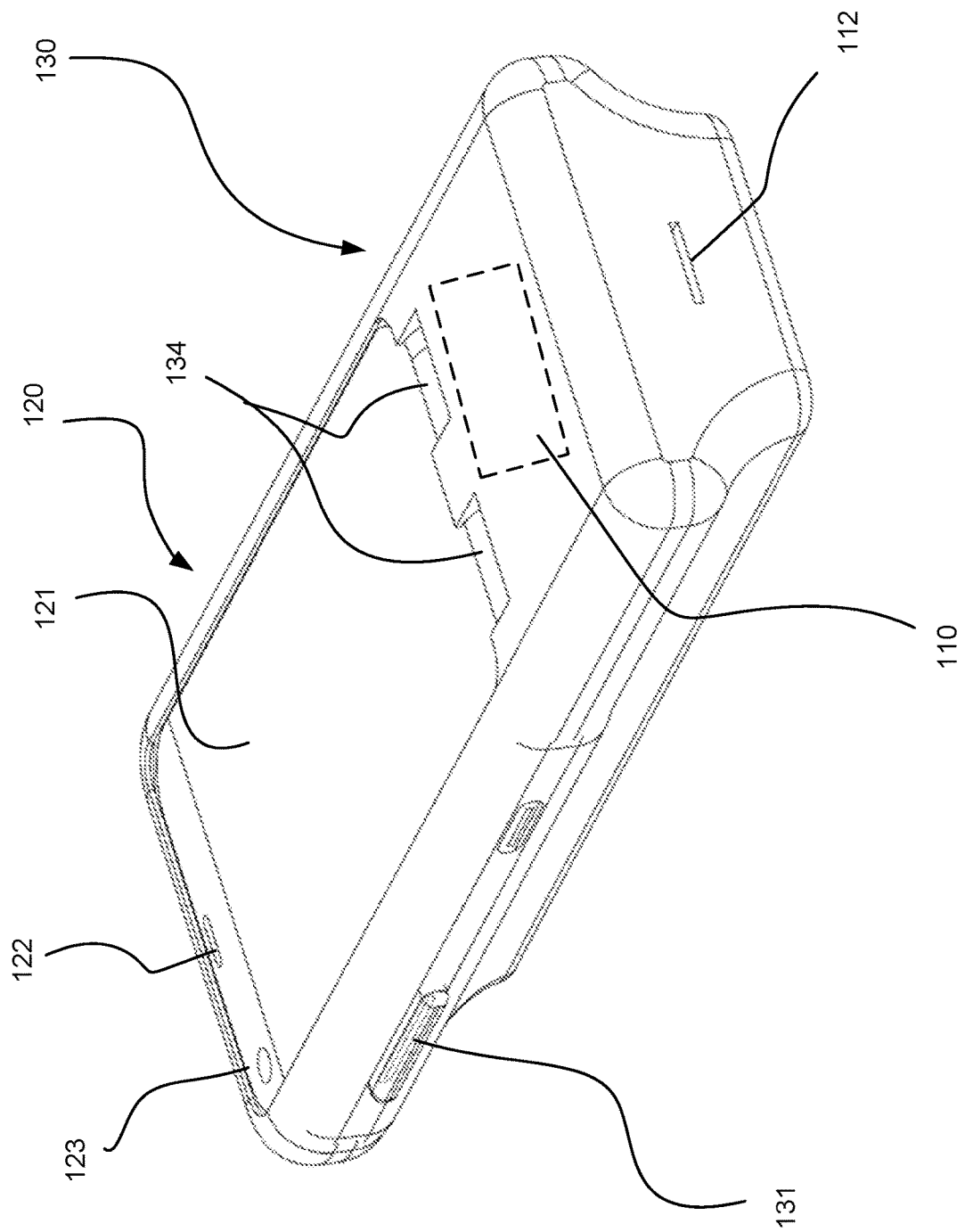
FIG. 1A illustrates a perspective view of a glucose monitoring system, according to an embodiment.

Methods, devices and systems related to managing health conditions as disclosed herein will become better understood through a review of the following detailed description in conjunction with the figures. The detailed description and figures provide merely examples of the various embodiments described herein. Those skilled in the art will understand that the disclosed examples may be varied, modified, and altered and not depart from the scope of the embodiments described herein. Many variations are contemplated for different applications and design considerations; however, for the sake of brevity, the contemplated variations may not be individually described in the following detailed description.

Throughout the following detailed description, example embodiments of various methods, devices and systems for managing health conditions are provided. Related elements in the example embodiments may be identical, similar, or dissimilar in different examples. For the sake of brevity, related elements may not be redundantly explained in multiple examples except to highlight dissimilar features. Instead, the use of a same, similar, and/or related element names and/or reference characters may cue the reader that an element with a given name and/or associated reference character may be similar to another related element with the same, similar, and/or related element name and/or reference character in an example embodiment explained elsewhere herein. Elements specific to a given example may be described regarding that particular example embodiment. A person having ordinary skill in the art will understand that a given element need not be the same and/or similar to the specific portrayal of a related element in any given figure or example embodiment in order to share features of the related element.

As used herein "same" means sharing all features and "similar" means sharing a substantial number of features or sharing materially important features even if a substantial number of features are not shared. As used herein "may" should be interpreted in the permissive sense and should not be interpreted in the indefinite sense. Additionally, use of "is" regarding embodiments, elements, and/or features should be interpreted to be definite only regarding a specific embodiment and should not be interpreted as definite regarding the invention as a whole. Furthermore, references to "the disclosure" and/or "this disclosure" refer to the entirety of the writings of this document and the entirety of the accompanying illustrations, which extends to all the writings of each subsection of this document, including the Title, Background, Brief description of the Drawings, Detailed Description, Claims, and Abstract.

Where multiples of a particular element are shown in a FIG., and where it is clear that the element is duplicated throughout the FIG., only one label may be provided for the element, despite multiple instances of the element being present in the FIG. Accordingly, other instances in the FIG. of the element having identical or similar structure and/or function may not be redundantly labeled. A person having ordinary skill in the art will recognize based on the disclosure herein redundant and/or duplicated elements of the same FIG. Despite this, redundant labeling may be included where helpful in clarifying the structure of the depicted example embodiments.

A conventional system and/or method for managing health conditions, such as diabetes, includes a measurement component (e.g., a glucometer) that measures an analyte (e.g., blood glucose) of a user. The measurement component may take a measurement of the analyte invasively, minimally and/or invasively The measurement component may include an analysis component to determine an amount of the analyte (e.g., blood glucose level) based on the measurement. In some instances, measurements determined by the measurement component are transmitted to a user's personal device, such a cell phone. The measurement data may be displayed and/or tracked on the personal device. Other measurements corresponding to the health condition of the user may be received, at the user's personal device, from other measurement devices (e.g., thermometer, scale, etc.) to facilitate in tracking the user's health condition.

Typically, to provide a blood sample for the measurement component, the user is pricked by a lancet to draw blood to measure the analyte. The blood is provided on a test strip. The test strip is placed into the measurement component to determine the amount of glucose in the blood that is subsequently displayed to the user. Such invasive systems are annoying, if not repugnant, to individuals with diabetes. Lancet pricks are not only painful but depending on the frequency required and the specific user's sensitivity to the pricks, can cause ongoing discomfort and pain for the user. Moreover, frequent use of a large number of lancets and/or test strips (e.g., multiple times per day) may lead to the spread of disease by a careless user. In addition to the physical discomfort and possible spread of disease, as described above, the individual is burdened with managing the availability and/or location of the numerous lancets, test strips, glucometer and personal device. As such, individuals may dread the process enough to avoid it completely which may lead to poor management of the health condition. As a result, the individual may experience severe symptoms due to poor management.

Implementations of the disclosure address the above-mentioned deficiencies and other deficiencies by providing methods, systems, devices, or apparatuses for glucose monitoring. In one embodiment, an integrated glucose monitoring system includes a mobile device, a glucose measuring device and a housing. The housing surrounds and the mobile device and the glucose measuring device. Accordingly, the integrated glucose monitoring system is a single unitary device for monitoring health conditions of an individual.

FIG. 1A depicts a perspective view of a glucose monitoring system 100 (also referred herein as a "system 100") for monitoring health conditions of a user, according to various embodiments. The user of system 100 may have a health condition, such as diabetes, that is monitored via system 100 which is described in further detail herein.

Referring to FIG. 1A, system 100, in various embodiments, includes measurement device 110 communicatively coupled to mobile device 120, where measurement device 110 and mobile device 120 are housed in housing 130. Accordingly, system 100, in various embodiments, is an integral device that includes various sub-components for monitoring health conditions (e.g., diabetes) of an individual. That is, the combination of measurement device 110, mobile device 120 and housing 130 form a single solitary glucose monitoring system.

The measurement device 110 includes a port 112 to receive a test strip that includes a sample of blood. In various embodiments, the measurement device 110 is a glucometer. A glucometer (also referred to as a glucose meter or blood glucose monitoring device herein) takes measurements of a blood sample of an individual to determine the amount of glucose (sugar) in the sample of blood. In general, to generate a blood glucose measurement, a person pricks their skin with a lancet. A blood sample (from the area of the pricked skin) is provided on a test strip. The portion of the test strip that includes the blood sample is then inserted into port 112. The measurement device 110 may generate glucose measurement data. The glucose measurement data may be then transmitted to the mobile device 120 for analyzation.

In various embodiments, the glucose measurement data is transmitted to the mobile device 120 via a wired connection between mobile device 120 and measurement device 110. The wired connection may be via a Universal Serial Bus (USB) protocol, Serial ATA (SATA) protocol, Peripheral Component Interconnect (PCI), and the like.

Figure 1B:
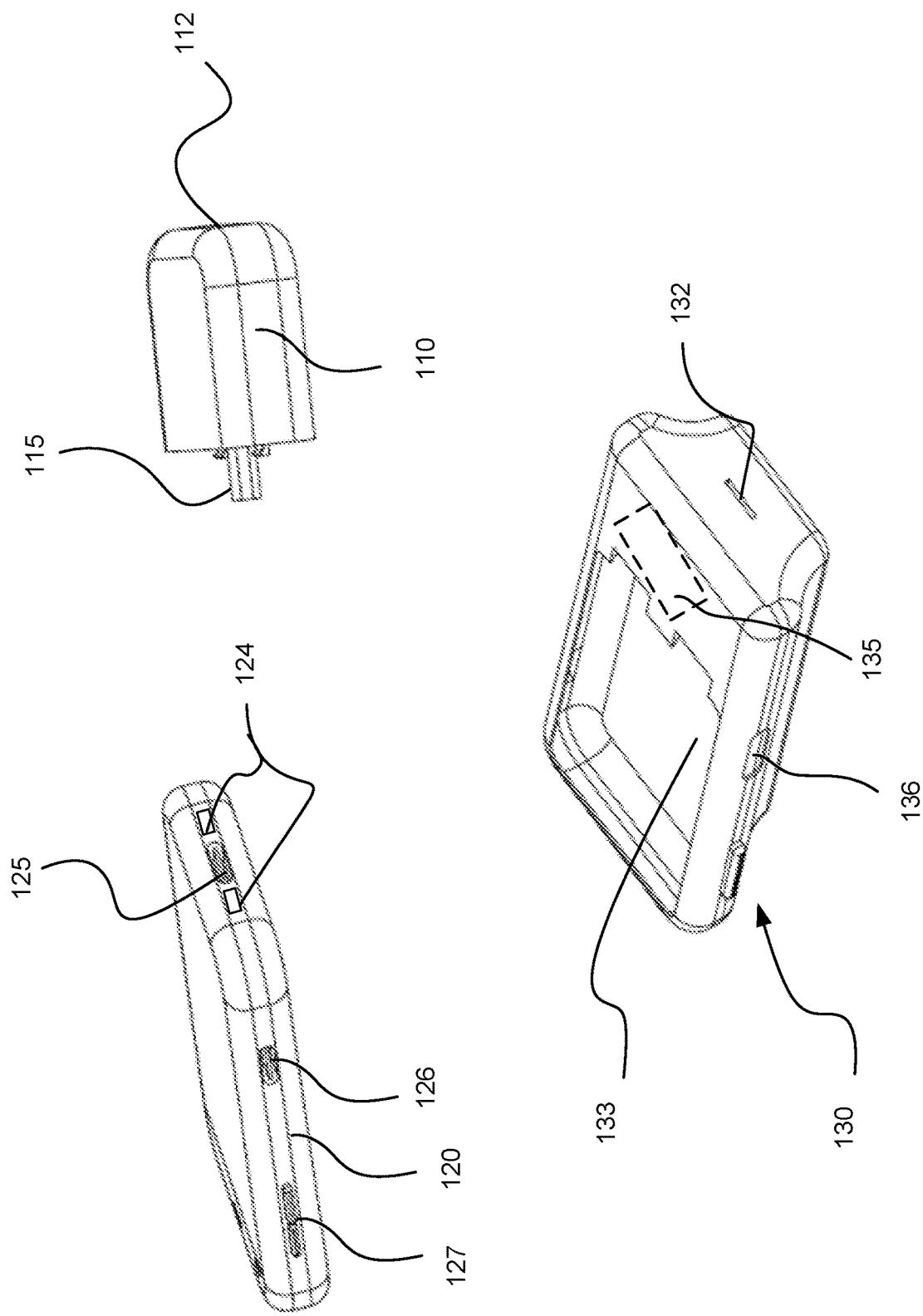
FIG. 1B illustrates an exploded view of the glucose monitoring system illustrated in FIG. 1A, according to an embodiment.

FIG. 1B is an exploded perspective view of system 100, according to an embodiment. Some of the features in FIG. 1B are the same as or similar to some of the features in FIG. 1A as noted by same and/or similar reference characters, unless expressly described otherwise. Furthermore, the elements and/or features described regarding FIG. 1B may be the same as and/or similar to other similarly named elements and/or features described and/or illustrated throughout this disclosure.

In particular, FIG. 1B shows the individual sub-components of system 100. The sub-components of system 100 are measurement device 110, mobile device 120 and housing 130.

Mobile device 120 may be modified (e.g., modified post-production) to provide appropriate functionality when implemented in system 100. In one embodiment, mobile device 120 may be modified to include a second port, such as port 126.

Port 126, in various embodiments, is a charging port to charge mobile device 120. It should be appreciated that port 125 is a charging port to charge mobile device 120. However, when mobile device 120 is seated in cavity 133 (and port 115 of measurement device 110 is seated within port 125 of the mobile device 120) port 125 is not accessible to charge mobile device 120. Port 126 may be accessed to charge mobile device 120 when port 125 is not accessible. In various embodiments, port 126 is the same type of port as port 125 (e.g., a USB-C port). Alternatively, port 126 is a different type of port as port 125.

Port 126 may be wired to a power management component of mobile device 120 (e.g., power management component 322). As such, both port 125 and port 126 are communicatively coupled to the power management component to manage the power for mobile device 120. Moreover, port 125 and 125 may facilitate in managing the power of measurement device 110.

Figure 1C:
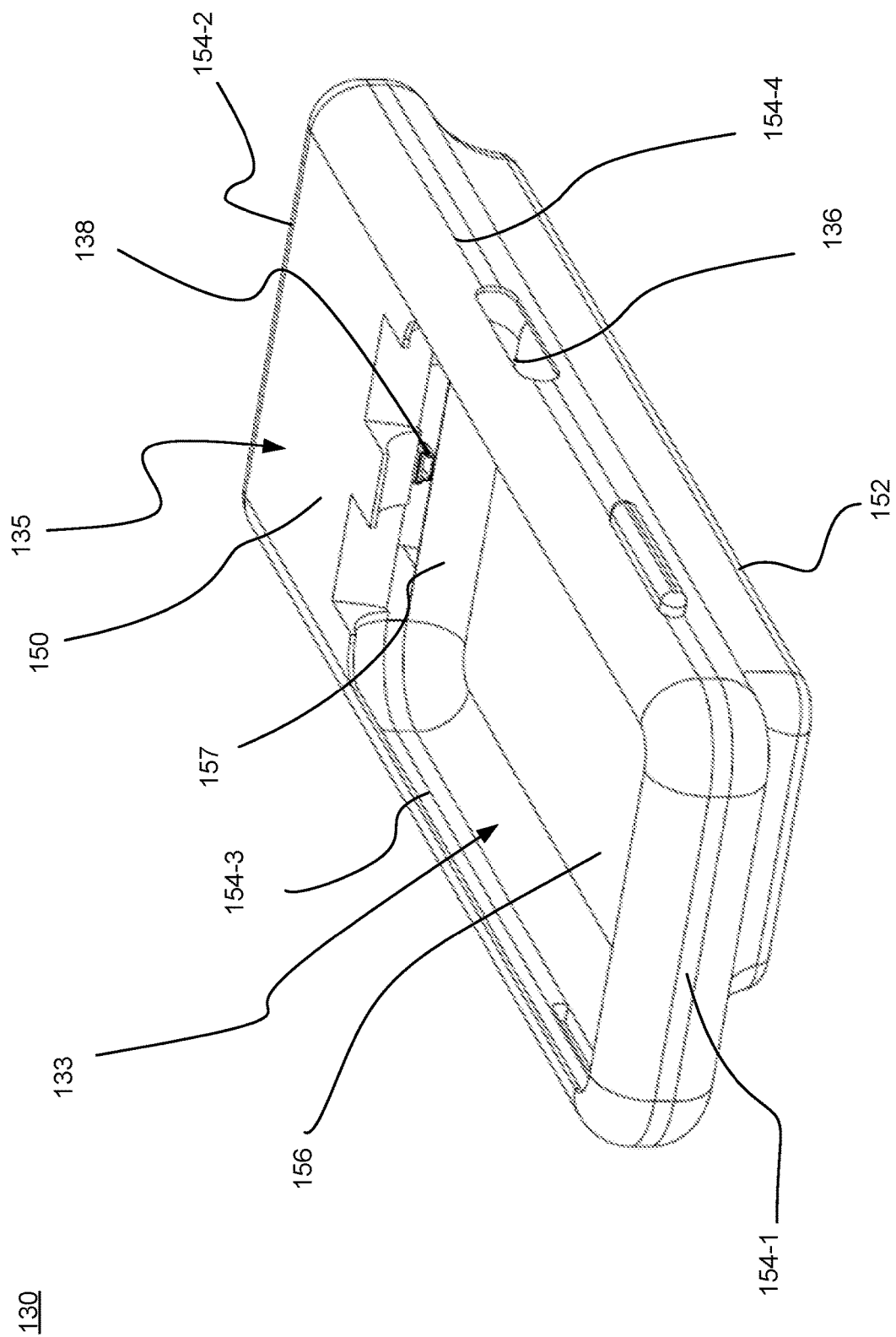
FIG. 1C illustrates a perspective view of a housing of the glucose monitoring system illustrated in FIG. 1A, according to an embodiment.

FIG. 1C depicts a perspective view of an embodiment of housing 130, according to an embodiment. Some of the features in FIG. 1C are the same as or similar to some of the features in FIGS. 1A-B as noted by same and/or similar reference characters, unless expressly described otherwise. Furthermore, the elements and/or features described regarding FIG. 1C may be the same as and/or similar to other similarly named elements and/or features described and/or illustrated throughout this disclosure.

Housing 130 includes a front wall 150 (e.g., a front surface) and a back wall 152 (e.g., a back surface) that is opposite the front wall 150. The housing 130 includes a number of lateral walls to form a perimeter of the housing 130. For example, the housing 130 includes wall 154-1 and wall 154-2 that is opposite wall 154-1. Additionally, the housing 130 includes wall 154-3 disposed between and wall 154-4 that is opposite wall 154-3.

The housing 130 includes intermediary wall 156 that is disposed between and parallel with wall 150 and wall 152. Wall 156 extends laterally between wall 154-3 and wall 154-4. Wall 156 extends longitudinally between walls 154-1 and 154-2.

Housing 130 includes internal wall 157 that is disposed between wall 154-1 and wall 154-2. Wall 157 physically separates cavity 133 (to house mobile device 120) and cavity 135 (to house measurement device 110). Wall 157 includes aperture 138 to provide physical access between cavity 133 and cavity 135. For example, measurement device 110 may be communicatively coupled to mobile device 120 via aperture 138.

Housing 130 includes cavity 133 is a substantially open cavity that is configured to house mobile device 120. Cavity 133 is formed within wall 154-1, wall 156, wall 157, wall 154-3 and wall 154-4. Housing 130 includes cavity 135 that is a substantially closed cavity to house measurement device 110. Cavity 135 is formed within wall 150, wall 156, wall 157, wall 154-2, wall 154-3, and wall 154-4.

Referring to FIGS. 1A-C, measurement device 110, in various embodiments, is integral with housing 130. That is, in one embodiment, measurement device 110 is embedded within cavity 135 of housing 130 and is not able to be removed from cavity 135 of housing 130 without physically modifying (e.g., tearing, cutting, breaking, etc.) the housing. In one embodiment, housing 130 is molded around measurement device 110 such that the measurement device is embedded within cavity 135 of housing 130.

Figure 1D:
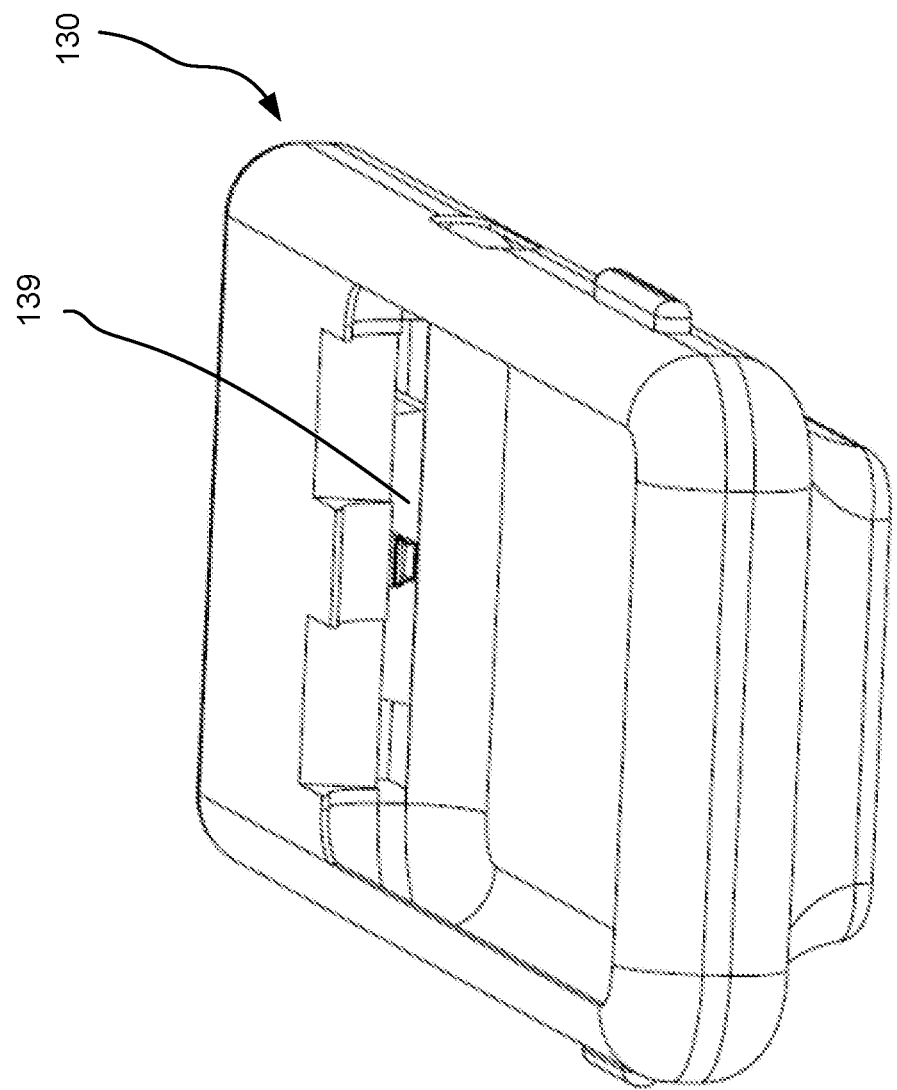
FIG. 1D illustrates a perspective view of a housing of the glucose monitoring system illustrated in FIG. 1A, according to an embodiment.

FIG. 1D depicts a perspective view of a housing of the glucose monitoring system 100, according to an embodiment. Some of the features in FIG. 1D are the same as or similar to some of the features in FIGS. 1A-C as noted by same and/or similar reference characters, unless expressly described otherwise. Furthermore, the elements and/or features described regarding FIG. 1D may be the same as and/or similar to other similarly named elements and/or features described and/or illustrated throughout this disclosure.

Alternatively, in various embodiments, measurement device 110 is releasably affixed within housing 130. For example, housing 130 includes aperture 139. Measurement device 110 is inserted into cavity 135 in housing 130 via aperture 139. Accordingly, measurement device 110 may be inserted into cavity 135 via aperture 139 and removed from the cavity in housing 130 via aperture 139. It is noted that aperture 138 (see FIG. 1C) may have smaller dimensions (e.g., height and/or width) than aperture 139. As such, measurement device 110 may be inserted into cavity 135, as described above, and is not able to be inserted into cavity 135 via aperture 138 (and not able to be removed from cavity 135 via aperture 138).

Measurement device 110 is communicatively coupled to mobile device 120. For example, port 115 of measurement device 110 extends through aperture 138 (or aperture 139) and is coupled to port 125 of mobile device 120.

Port 125 is configured to send data to and receive data from measurement device 110. Additionally, port 125 is configured to provide power to measurement device 110. In various embodiments, port 125 is a USB port (e.g., USB-C port, USB-micro port, USB-mini port) mated with a respective USB port (e.g., port 115) of measurement device 110.

Mobile device 120, in various embodiments, includes, among other things, display 121 (e.g., a touch display), microphone 122, camera 123, speaker 124, and port 125. As depicted, in at least FIGS. 1A-C, mobile device 120 is releasably affixed in cavity 133. For example, mobile device 120 may be inserted into cavity 133 and retained within walls 154-1, 154-3, 154-4 and 157 via a friction fit. The mobile device may then be removed from within cavity 133 (and also detached from measurement device 120). In one embodiment, display 121 is co-planar with wall 150 when the mobile device is seated within cavity 133.

In another embodiment, mobile device 120 is modified (e.g., modified post-production) to include coupling features configured to releasably couple to measurement device 110. For example, mobile device 120 is modified to include latching features 221 and 222, described in further detail below.

Referring to FIGS. 2A-F, in various embodiments, measurement device 110 and mobile device 120 are releasably coupled to one another via various latching means (e.g., snap fit, friction fit, cantilever hook, and the like). For example, measurement device 110 includes latching features 211 and 212 that are resiliently coupled to latching features 221 and 222 of mobile device 120, respectively. Some of the features in FIGS. 2A-F are the same as or similar to some of the features in FIGS. 1A-D as noted by same and/or similar reference characters, unless expressly described otherwise. Furthermore, the elements and/or features described regarding FIGS. 2A-F may be the same as and/or similar to other similarly named elements and/or features described and/or illustrated throughout this disclosure.

In one embodiment, latching feature 211 (and similarly latching feature 212) is a cantilever (e.g., a flange) with a hook feature disposed at a distal end. Latching feature 211 deflects (e.g., bends) when engaging feature 221 of mobile device 120 and subsequently connects (e.g., snaps) with feature 221. That is, for example, latching feature 211 is a resilient feature that bends from an initial position and "snaps" back to its original position after engaging with feature 221. As a result, measurement device 110 is physically retained/coupled with mobile device 120. Measurement device 110 may be decoupled from mobile device 120 by uncoupling the latching features of measurement device 110 with the corresponding latching features of mobile device 120. The latching features of mobile device 120 and measurement device 110 may be able to pass through wall 157 via one or more apertures (e.g., aperture 138 or aperture 139).

Figure 2A:
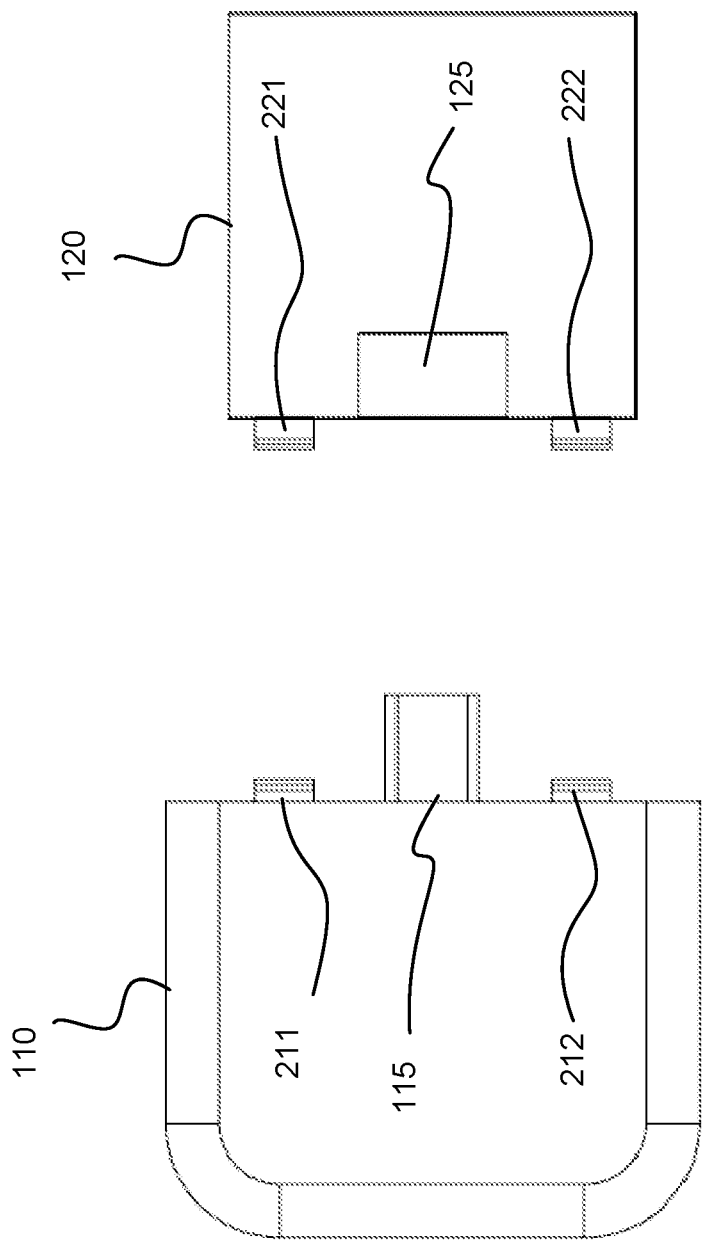
FIG. 2A illustrates a plan view of a mobile device and a glucose monitor in a detached state, according to an embodiment.
Figure 2B:
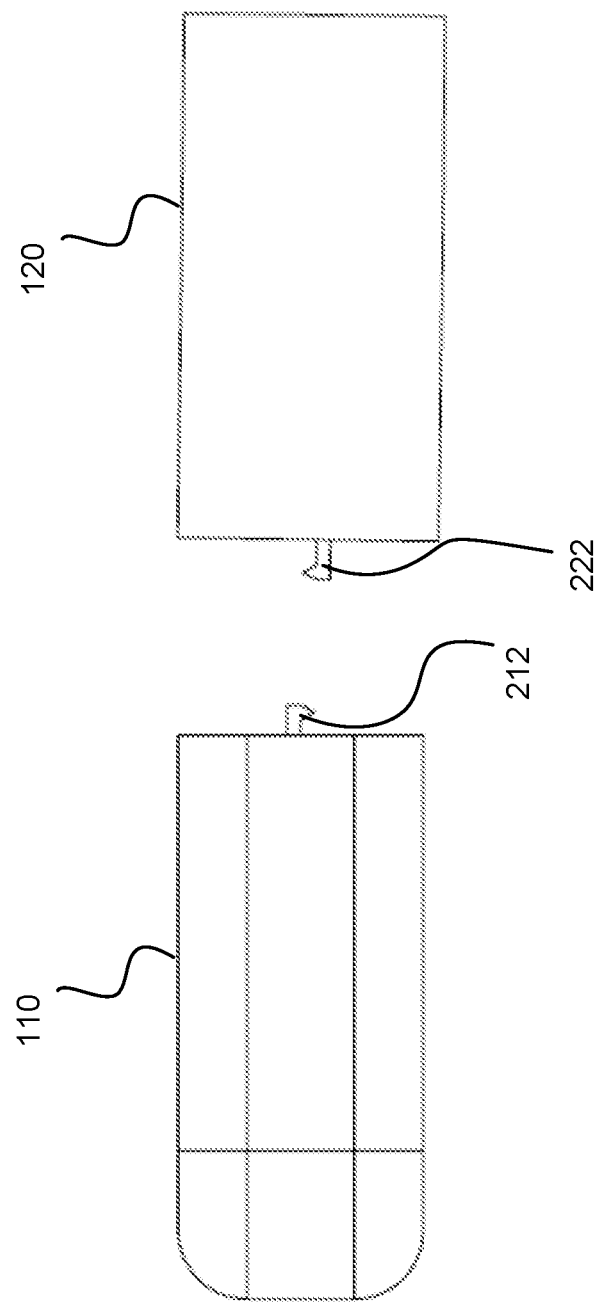
FIG. 2B illustrates a side view of the mobile device and the glucose monitor in the detached state, according to an embodiment.
Figure 2C:
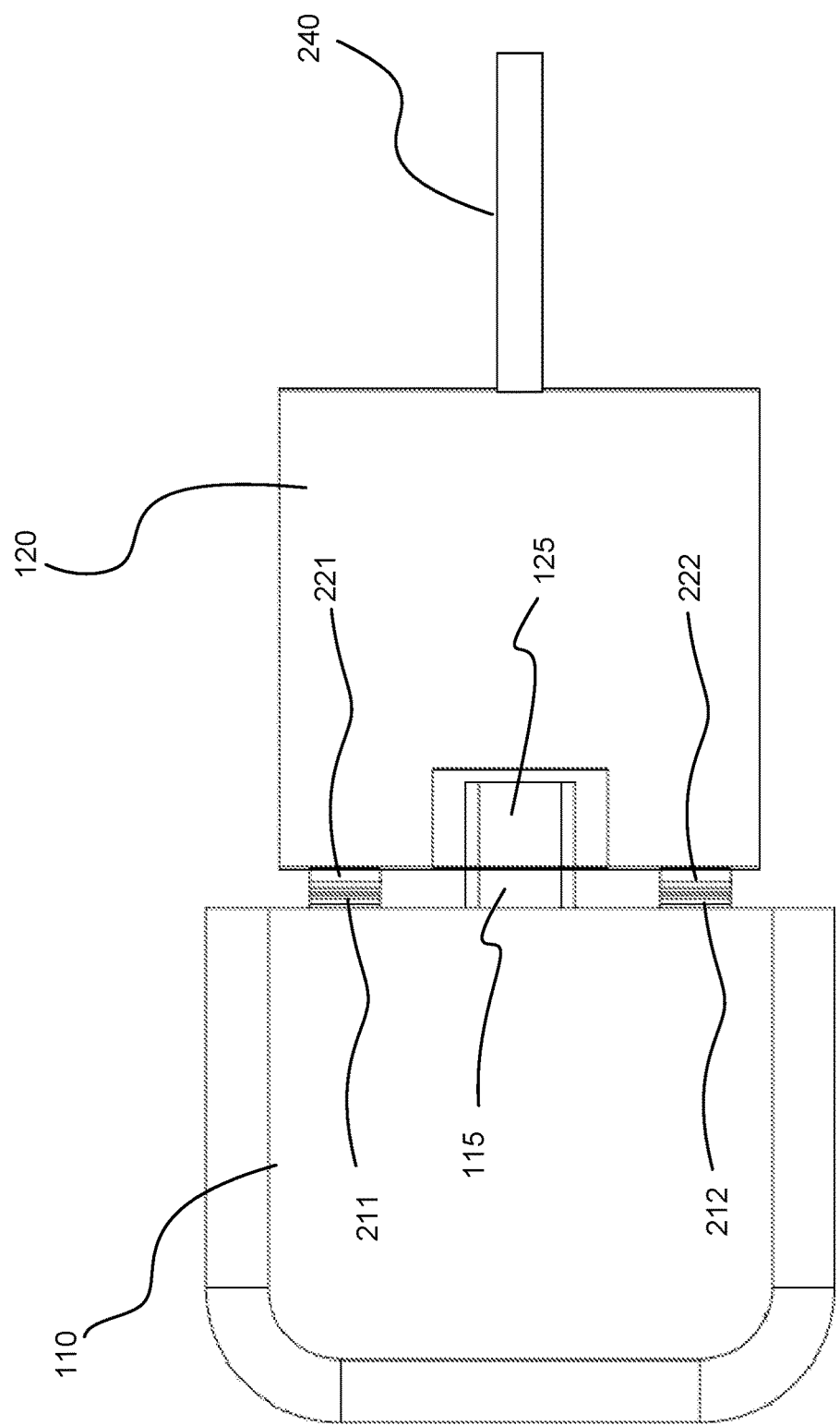
FIG. 2C illustrates a plan view of the mobile device coupled to the glucose monitor, according to an embodiment.

Specifically, FIG. 2C depicts an embodiment of mobile device 120 coupled with measurement device 110. For example, port 215 of measurement device 110 is coupled to port 125 of mobile device 120. As such, data is able to be transmitted from measurement device 110 to mobile device 120 (or vice versa). Additionally, in one embodiment, power signals are able to be transmitted from mobile device 120 to measurement device 110 to provide power to measurement device 110.

In one embodiment, measurement device 110 receives test strip 240 that includes a sample of blood. As such, measurement data generated by measurement device 110 may be transmitted to mobile device 120 when port 125 and port 115 are coupled together.

Figure 2E:
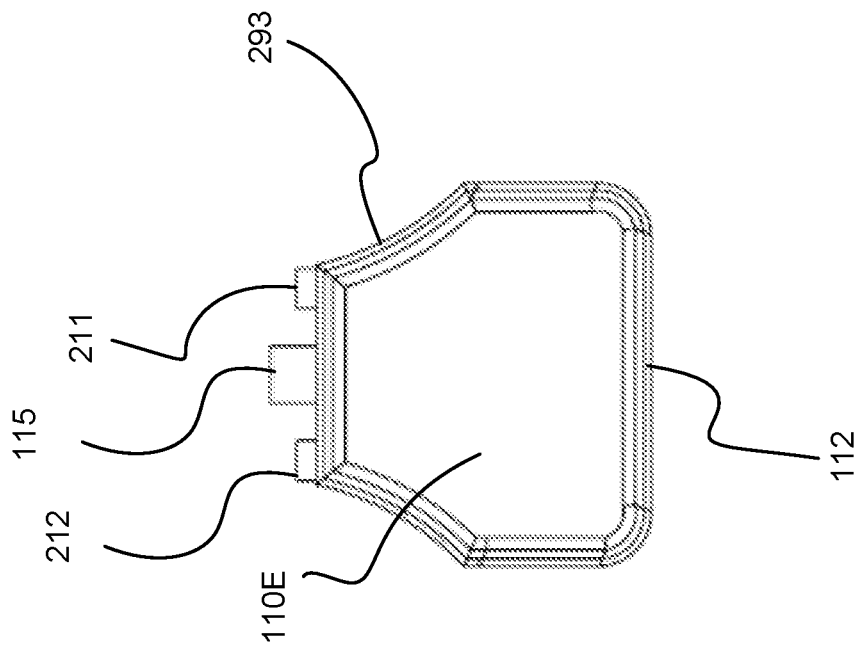
FIG. 2E illustrates a plan view of a glucose monitor, according to an embodiment.
Figure 2D:
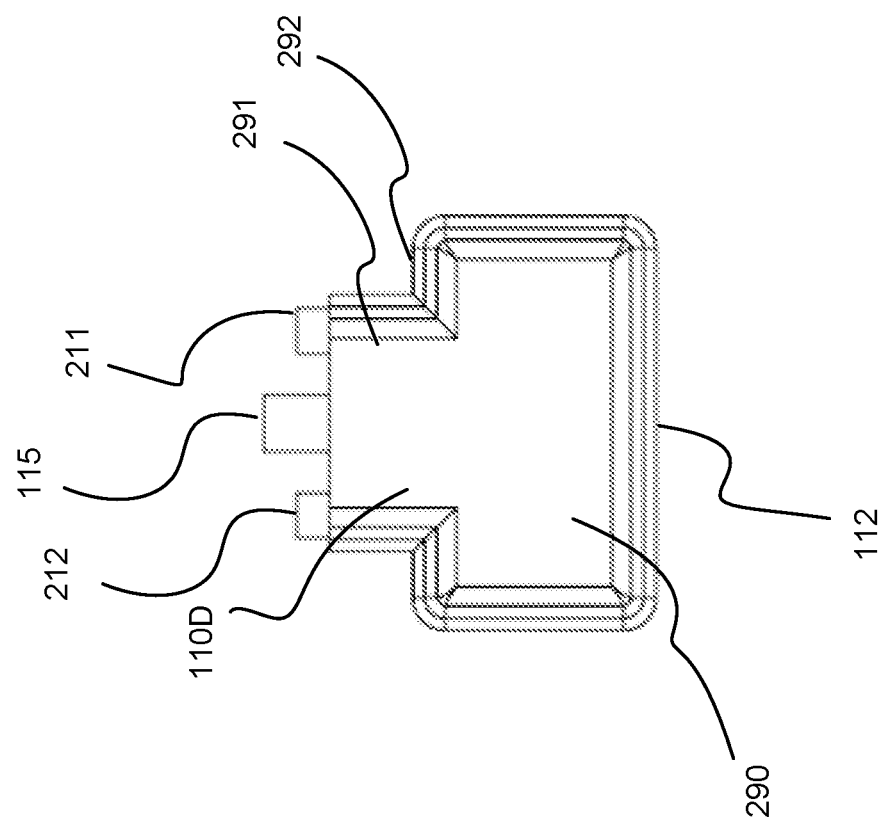
FIG. 2D illustrates a plan view of a glucose monitor, according to an embodiment.

FIGS. 2D-E depict embodiments of a measurement device. In particular, FIG. 2D depicts a top view of measurement device 110D, according to an embodiment. Measurement device 110D, in one embodiment, includes a first portion 290 that is substantially rectangular and a second portion 291 that is substantially rectangular. Measurement device 110D includes wall 292 that enables a person to grip measurement device 110D and pull measurement device 110D away from a mobile device connected to measurement device 110D.

FIG. 2E depicts a top view of measurement device 110E, according to an embodiment. Measurement device 110E is non-rectangular. Measurement device 110E includes wall 293 that enables a person to grip measurement device 110E and pull measurement device 110E away from a mobile device connected to measurement device 110E.

Figure 2F:
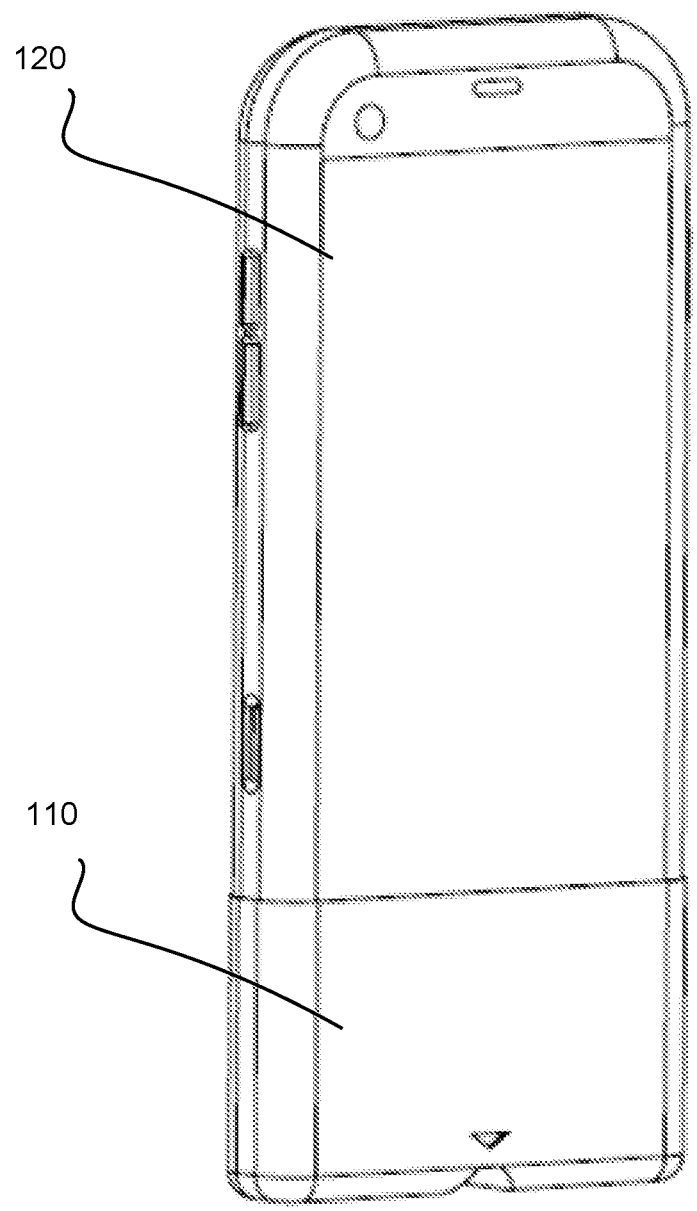
FIG. 2F illustrates a perspective view of a mobile device coupled to a glucose monitor, according to an embodiment.

FIG. 2F depicts an isometric view of an embodiment of system 100F that includes measurement device 110 coupled to mobile device 120, according to an embodiment. For clarity and brevity, housing 130 is not depicted in FIG. 2F.

Referring again to FIGS. 1A-D, housing 130 includes various features to facilitate in the functioning of mobile device 120 and measurement device 110. For example, housing 130 includes buttons 131 that are proximate to and correspond with volume control buttons 127 of mobile device 120. Accordingly, when a user depresses buttons 131 on housing 130, buttons 131 depress buttons 127 of mobile device 120. Similarly, housing 130 may include a power button that is physically proximate a power button on mobile device 120. Accordingly, the power button on the cellular phone is depressed in response to the user depressing the corresponding power button of housing 130.

Housing 130 includes various apertures to facilitate in the functioning of mobile device 120 and measurement device 110. For example, housing 130 includes aperture 136 that allows access to port 126 of mobile device 120, and aperture 132 that allows access to port 112 (e.g., a test strip port) of measurement device 110.

In various embodiments, housing 130 includes apertures 134 that physically correspond to speakers 124 of mobile device 120. Apertures 134 allow sound to be emitted unimpeded from speakers 124 while mobile device 120 is seated within housing 130.

Housing 130 may be comprised of any material to appropriately protect and house mobile device 120 and measurement device 110. For example, housing 130 may include various plastic, rubber or the like.

Figure 3:
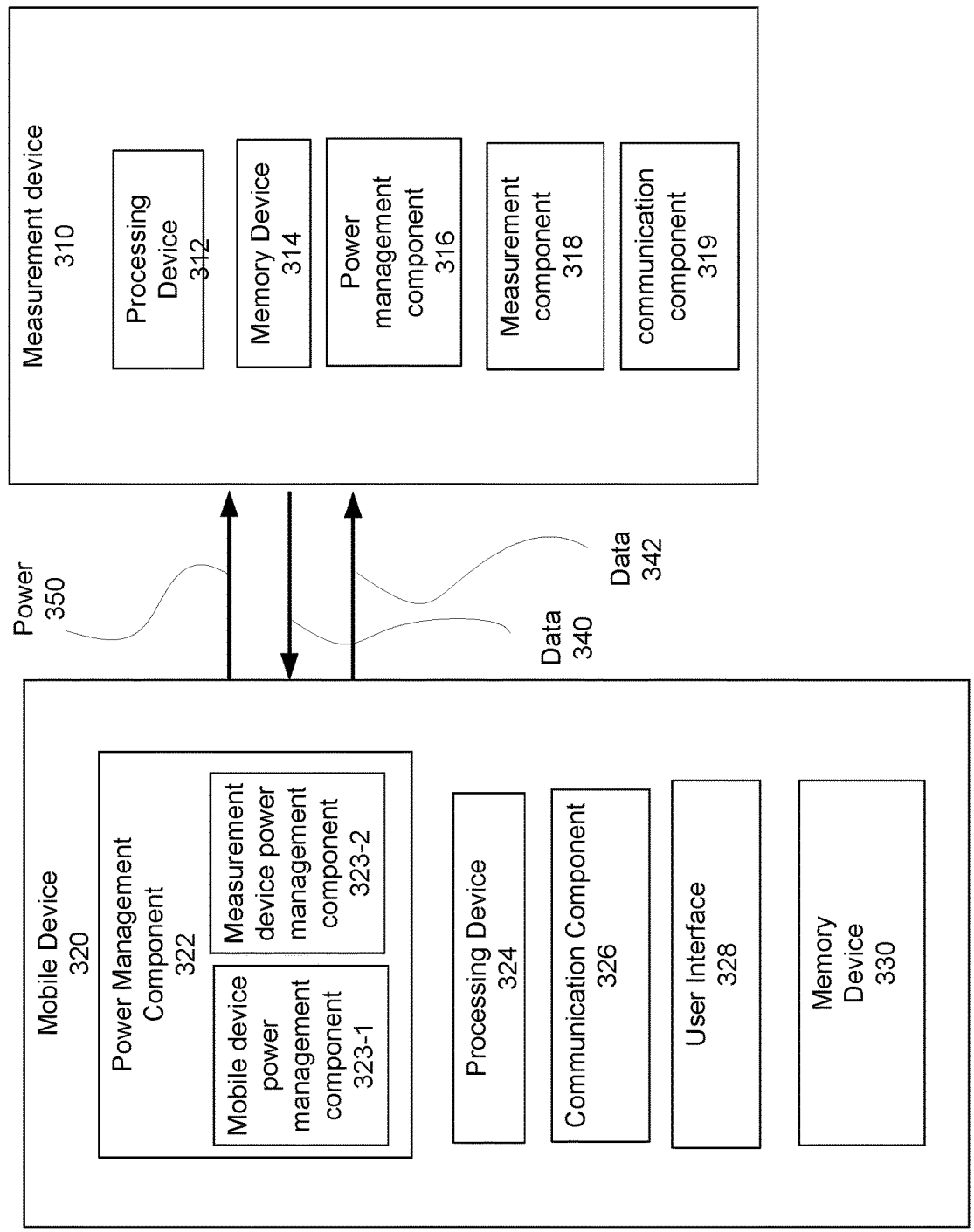
FIG. 3 illustrates a block diagram of a glucose monitoring system, according to an embodiment.

FIG. 3 depicts a block diagram of system 300, according to an embodiment. System 300 may be similar to system 100, as described herein. Some of the features in FIG. 3 are the same as or similar to some of the features in FIGS. 1A-2F as noted by same and/or similar reference characters, unless expressly described otherwise. Furthermore, the elements and/or features described regarding FIG. 3 may be the same as and/or similar to other similarly named elements and/or features described and/or illustrated throughout this disclosure. System 300 includes measurement device 310 (e.g., measurement device 110) and mobile device 320 (e.g., mobile device 120).

Measurement device 310 may generate and communicate data about an analyte associated with a user, such as an individual within whom the analyte may be found. The analyte may include a physiological element, including bodily fluid, blood, interstitial fluid, blood glucose, platelets, red blood cells, white blood cells, water, sebum, fatty tissue, muscle tissue, bone, nerve tissue, a hormone, glandular fluid, ligament tissue, cartilage, and so forth.

Measurement device 310 includes processing device 312, memory 314, power management component 316, measurement component 318, and communication component 319.

Measurement component 318 may invasively take a measurement of an analyte of the user by invasive means. For example, the user's skin is punctured and/or the analyte is withdrawn from the user. In an embodiment, measurement component 318 may include an analyte collection mechanism for collecting body fluid and/or tissue containing the analyte (e.g., a test strip), and a measurement mechanism for measuring the analyte. The measurement mechanism may include a chemical reactant and electrodes in the test strip. The measurement mechanism may generate electronic signals corresponding to the analyte reacting with the chemical reactant.

In one embodiment, measurement device 310 is an invasive glucometer. Blood of the user may be drawn from the punctured skin, and the blood may be placed on a test strip. An end of the test strip may be placed into measurement device 310, and processing device 312 may measure conductivity of the blood on the strip. The conductivity may indicate an amount of glucose in the user's blood. The amount of glucose (e.g., data 340) may be communicated to mobile device 320 via a USB connection.

Processing device 312 (and similarly processing device 324) may include various electronics for processing electronic signals generated by the measurement component and/or the communication component. In an embodiment, processing device 312 may include a processing device and a memory device (e.g., memory 314). The processing device may have persistent and/or transitory memory, and the memory device may have persistent and/or transitory memory. For example, the processing device may have transitory memory and the memory device may have persistent memory. The processing device may generate an output based on an input. For example, the processing device may receive an electronic signal from measurement component 318. Processing device 312 may send the signal to the memory device, and the memory device may store the signal. Processing device 312 may read the signal and perform one or more tasks with the signal, such as determining an amount of current associated with the signal. Processing device 312 may read from the memory device a quantity of the analyte corresponding with the amount of current. Processing device 312 may transmit a value associated with the quantity of the analyte to mobile device 320. At mobile device 320, user interface 328 may display the value to the user. In an embodiment, processing device 312 may transmit data 340 such as the value and/or the amount of the current to communication component 319, which may transmit data 340 to mobile device 320.

In various embodiments, processing device 312 may include, a microprocessor, a computer processing unit (CPU), a vision processing unit, a tensor processing unit, a neural processing unit, a physics processing unit, a digital signal processor, an image signal processor, a synergistic processing element, a field-programmable gate array (FPGA), a sound chip, a multi-core processor, and so forth. As used herein, "processor," "processing component," "processing device," and/or "processing unit" may be used generically herein to refer to any or all of the aforementioned specific devices, elements, and/or features of the processing component.

Communication component 319 (and similarly communication component 326) may include a networking device such as a networking chip, one or more antennas, and/or one or more communication ports. The networking device may generate radio frequency (RF) signals and transmit the RF signals to one or more of the antennas. The RF signals may be broadcast by the antennas. The networking device may generate electronic signals and transmit the RF signals to one or more of the communication ports. For example, communication component 319 transmits data 340 to mobile device 320. The electronic signals may be transmitted to a communication hardline by the communication ports. The networking device may generate optical signals and transmit the optical signals to one or more of the communication ports. The optical signals may be transmitted to a communication hardline by the communication port, and/or the optical signals may be transmitted across open space by the networking device.

In various embodiments, the communication component may include hardware and/or software for generating and communicating signals over a direct and/or indirect network communication link. For example, the communication component may include a USB port and a USB wire, and/or an RF antenna with Bluetooth™ programming installed on a processor, such as the processing component, coupled to the antenna. In another example, the communication component may include an RF antenna and programming installed on a processor, such as the processing component, for communicating over a Wifi and/or cellular network. As used herein, "communication device" and/or "communication component" may be used generically herein to refer to any or all of the aforementioned elements and/or features of the communication component.

Power management component 316, in various embodiments, is a microcontroller that governs power functions of measurement device 310. Power management component 316 is responsible for coordinating many functions of measurement device 310, such as, monitoring power connections and battery charges, charging batteries when necessary, controlling power to other integrated circuits, shutting down unnecessary system components when they are left idle, controlling sleep and power functions (on and off). In one embodiment, power management component 316 receives power 350 from mobile device 320 (e.g., from power management component 323-2). As such, measurement device 310 is powered primarily via mobile device 320.

Power management component 316, in various embodiments, may include a battery. The battery may be charged via power 350 provided by mobile device 320. In some instances, mobile device 320 may not actively provide power to measurement device 310. As such, the battery may provide the requisite power to measurement device 310.

Mobile device 320 may be any mobile electronic device such as a mobile cellular phone, tablet and the like. For example, mobile device 320 may be a smart phone (e.g., an iPhone, Android phone, etc.). Mobile device 320 may include power management component 322, processing device 324, communication component 326, user interface 328, and/or memory device 330.

Communication component 326 may include hardware and/or software that may be configured to communicate data with another device, such as the cloud-based server, another mobile device, measurement device 310 and so on. In various embodiments, communication component 326 may be a transceiver. That is, communication component 326 can transmit data (e.g., transmit data 342 to measurement device 310) and receive data (e.g., receive data 340 from measurement device 310).

In one embodiment, processing device 324 generates data 342 and communication component 326 transmits data 342 to measurement device 310. Data 342 may be power information, such as when to turn the measurement device on/off, go into sleep mode, and the like.

Data 342 may be calibration data for measurement device 310. For example, measurement device 310 is calibrated corresponding to a first type of test strip. Prior to use of a second type of test strip, measurement device 310 needs to be calibrated to provide accurate results when the second type of test strip is used. Data 342 may be update information for measurement device 310. For example, data 342 updates software and/or firmware associated with various components (e.g., power management component, measurement component, etc.) of measurement device 310.

Power management component 322, in various embodiments, is a microcontroller that governs power functions of mobile device 320. In particular, in one embodiment, power management component 323-1 powers mobile device 320 and power management component 323-2 provides power 350 to measurement device 310. Power management component 322 is responsible for coordinating many functions of measurement device 322 (or measurement 310), such as, monitoring power connections and battery charges, charging batteries when necessary, controlling power to other integrated circuits, shutting down unnecessary system components when they are left idle, controlling sleep and power functions (on and off). In one embodiment, power management component 322 receives power from an external power source via port 125 and/or port 126. As described above, in some embodiments, power management component 322 provides power 350 to measurement device 310. Power management component 322, in various embodiments, may include a battery. The battery may be charged via the external power source.

User interface 328 may include a screen, buttons, a microphone, a speaker, and/or a touchscreen. User interface 328 may include hardware and/or software that may communicate information to the user and/or receive input from the user. The user interface may include one or more lights, a speaker, a display, one or more buttons, and so forth. In an embodiment, the user interface may include a touchscreen and a graphical user interface (GUI). In an embodiment, the user interface may include a light emitting diode (LED) display, a liquid crystal display (LCD), and so forth. The user interface may receive inputs from the user which may be transmitted to the processing component. Processing device 324 may generate an output based on the user inputs. For example, the input may include a request for a past measurement stored in the memory device. Processing device 324 may retrieve the past measurement and the user interface may display the past measurement to the user. As used herein, "user interface," "display," and/or "input device" may be used generically herein to refer to any or all of the aforementioned features and/or elements of the user interface.

Mobile device 320 may include an application that may communicate health information with the user. The health information may be health information of a patient. The user may be the patient, a health care provider such as a nurse, doctor, and/or physician's assistant, a health care insurer, a third party authorized by the patient to access the patient's health information such as an individual with power of attorney for the patient, a healthcare partner of the patient, and so forth. In an example, the healthcare partner may include a third party who reviews the patient's healthcare information and communicates with the patient about the patient's health. The healthcare partner may be an employee of a healthcare customer service center such as a call center.

Figure 4:
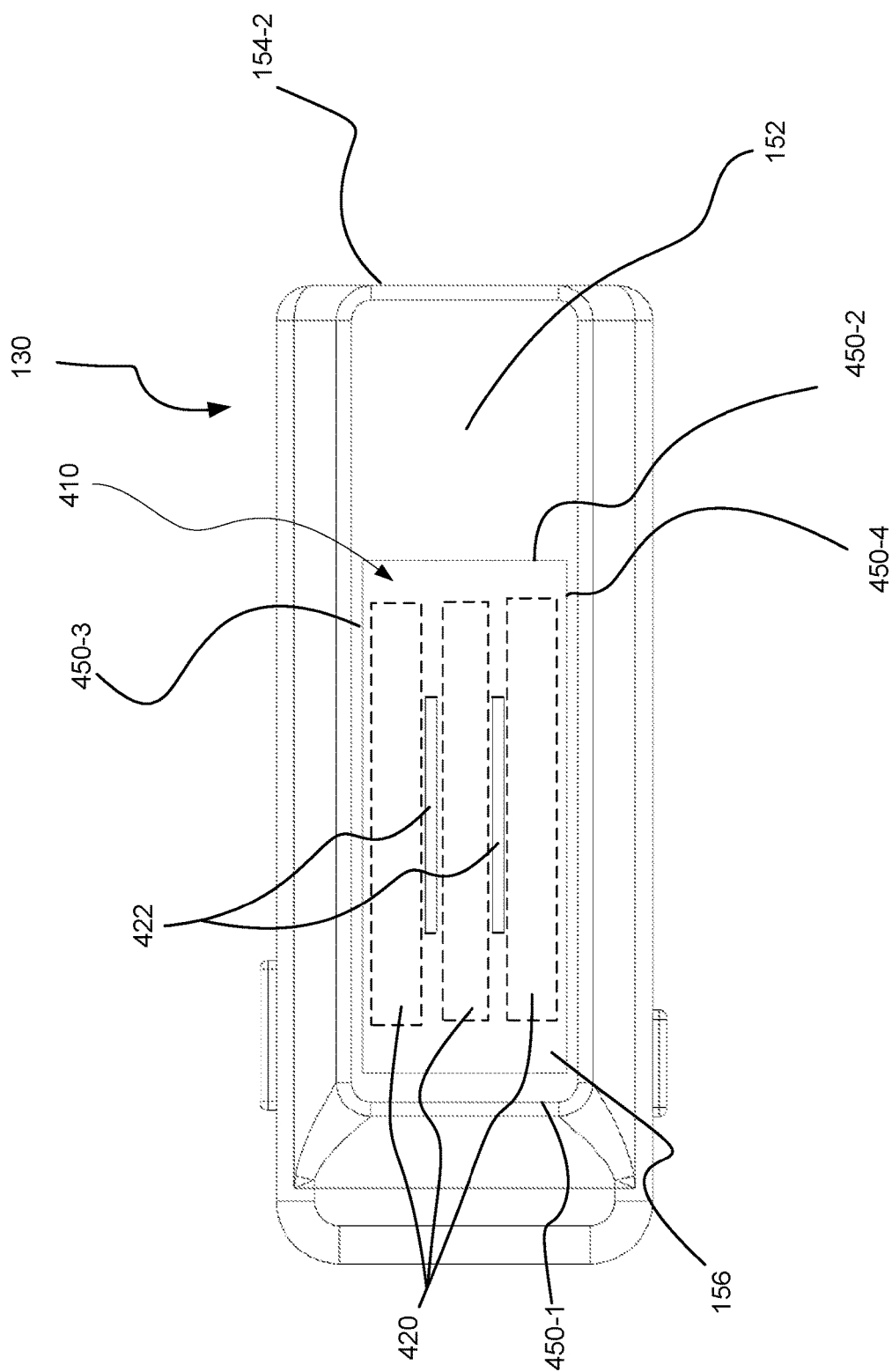
FIG. 4 illustrates a perspective of a back view of a housing of glucose monitoring system illustrated in FIG. 1A, accordingly to an embodiment.

FIG. 4 depicts a view of system 400, according to an embodiment. System 400 is similar to at least system 100 and system 300. Some of the features in FIG. 4 are the same as or similar to some of the features in FIGS. 1A-B and FIG. 3 as noted by same and/or similar reference characters, unless expressly described otherwise. Furthermore, the elements and/or features described regarding FIG. 4 may be the same as and/or similar to other similarly named elements and/or features described and/or illustrated throughout this disclosure. For example, system 400 includes housing 130, measurement device 110 and mobile device 120. In particular, FIG. 4 depicts a view of a back portion of housing 130.

Housing 130 includes cavity 410 to store various components 420 related to the testing of the user. Cavity 410 is formed within wall 156, wall 450-1, wall 450-2 (opposite wall 450-1), wall 450-3 and wall 450-4 (opposite wall 450-3).

Cavity 410, in various embodiments, is enclosed by a releasable cover. The cover may be coupled to housing 130 via a latching mechanism, press fit and the like.

Glucose testing may be burdensome to the user. For example, a user may need to do multiple glucose tests a day and manage all of the various components associated with the testing. In particular, the user needs to have the requisite testing supplies (e.g., lancets, test strips, cleaning supplies, etc.) to provide proper testing. Various supplies/components associated with glucose testing are stored in cavity 410 for easy access and management of the various supplies/components.

Components 420 may include one or more of a lancet, glucose test strips, sanitizer and the like. The sanitizer may be any sanitizer that cleans the skin at the location of the prick of the lancet. For example, the sanitizer may be alcohol-based wipes for wiping the location of the skin to be lanced (and/or lanced) by the lancet and/or a spray bottle for spraying an alcohol-based fluid at the location to be lanced (and/or lanced) by the lancet.

In various embodiments, a user may replace a component when it is depleted. For example, a user may replenish the glucose test strips in cavity 410 with additional glucose test strips.

Cavity 410 may include retaining features 422 for retaining components 420 within cavity 410. In one embodiment, retaining features 422 are tabs that protrude from wall 156. For example, a sanitizing bottle may be retained between one or more retaining features such that the sanitizing bottle is affixed within cavity 410. A user may grasp the sanitizing bottle from between the one or more retaining features and remove the bottle from cavity 410 for use by the user. Upon use, the user may then reinsert the bottle between the one or more retaining features.

Figure 5:
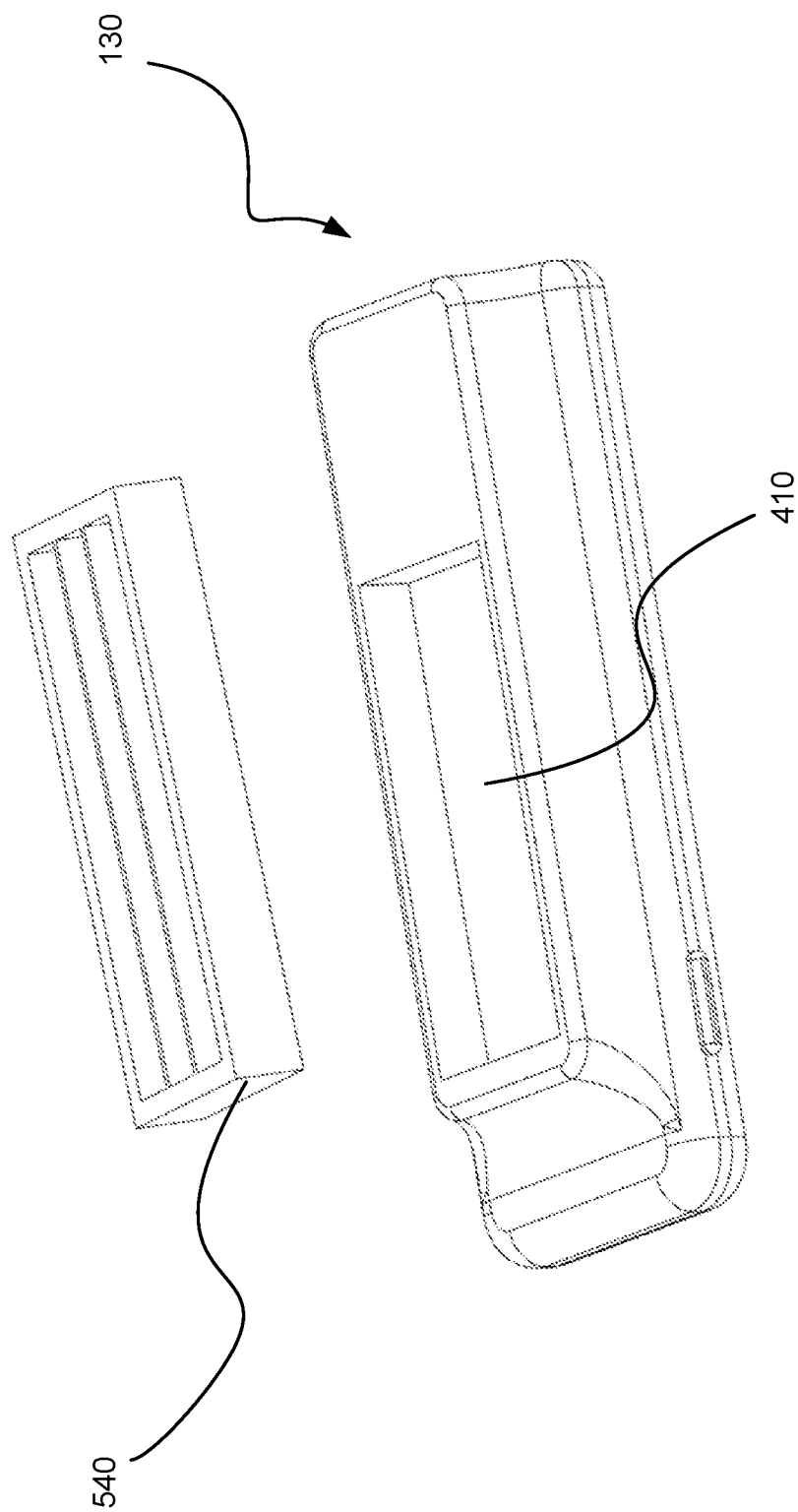
FIG. 5 illustrates an exploded view of a housing of a glucose monitoring system and glucose measuring components, accordingly to an embodiment.

FIG. 5 depicts a view of system 500. System 500 is similar to at least system 100, 300 and 400 described herein. Some of the features in FIG. 5 are the same as or similar to some of the features in FIGS. 1A-B, FIG. 3 and FIG. 4 as noted by same and/or similar reference characters, unless expressly described otherwise. Furthermore, the elements and/or features described regarding FIG. 5 may be the same as and/or similar to other similarly named elements and/or features described and/or illustrated throughout this disclosure. System 500 includes housing 130 and measurement device 110 and mobile device 120.

System 500 includes container 540 that is releasably seated into cavity 410. Container 540 may be releasably seated into cavity 410 by various means such as a snap fit, latching mechanism and the like. Container 540 includes components 420, as described above. Container 540 may be obtained (e.g., purchased) by the user and seated into cavity 410 by the user. In various embodiments, when one or more components of components 420 are depleted, container 540 is removed (or ejected) from cavity 410 and replaced with a new container (containing replenished components 420).

In one embodiment, when one or more components of components 420 is depleted, container 540 is removed (or ejected) from cavity 410 and replaced with another brand of container that includes the same, similar, or different components as compared to components 420. For example, container 540 includes lancets from a first brand and a replacement container includes lancets of a different brand. In another example, container 540 includes a lancet and testing strips and a replacement container includes multiple lancets and a sanitizer.

Figure 6A:
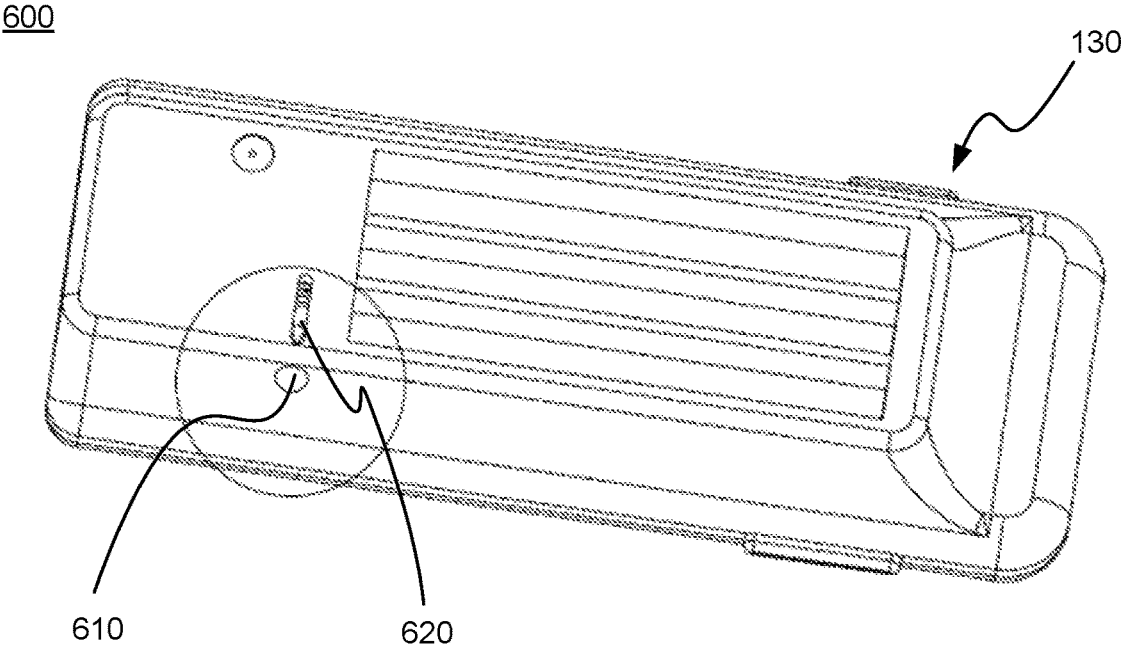
FIG. 6A illustrates a perspective back view of a housing with a lancet in a retracted position, accordingly to an embodiment.
Figure 6B:
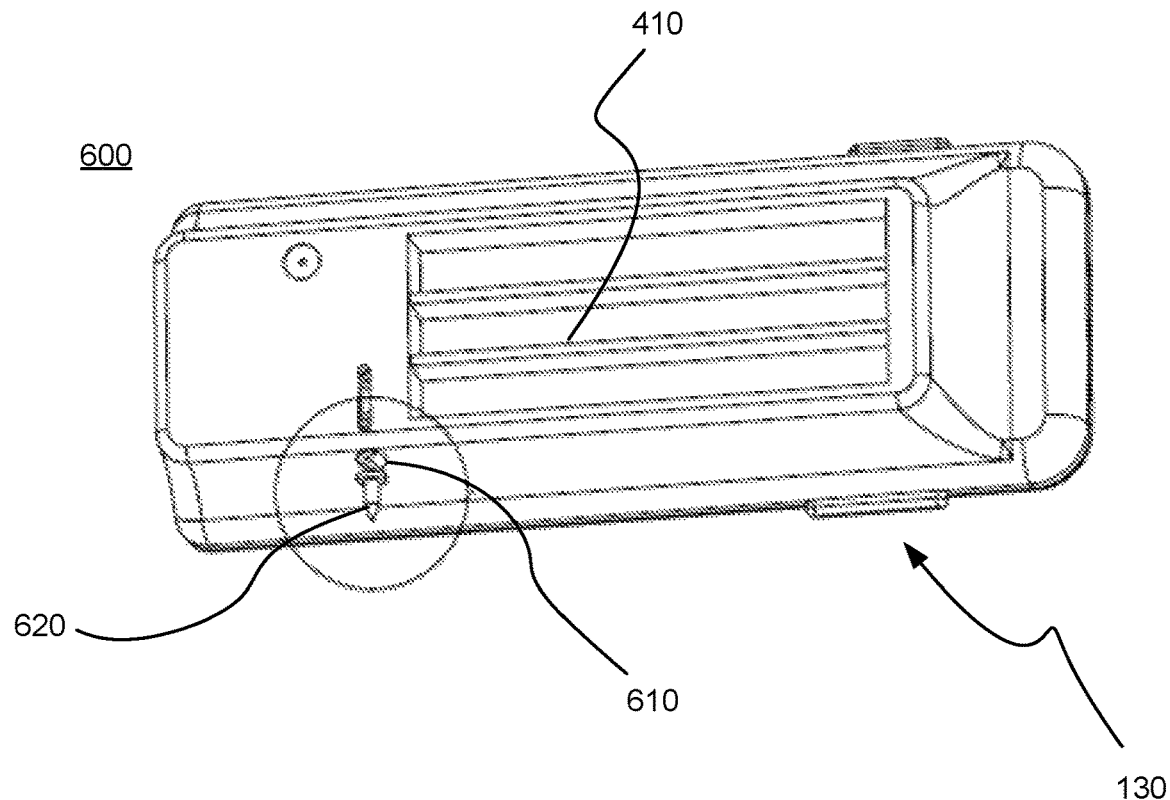
FIG. 6B illustrates a perspective back view of a housing with a lancet in an extended position, accordingly to an embodiment.

FIGS. 6A-B depict an embodiment of system 600. System 600 is similar to at least systems 100, 300, 400 and 500 described herein. Some of the features in FIGS. 6A-B are the same as or similar to some of the features in FIGS. 1A-B, and FIGS. 3-5 as noted by same and/or similar reference characters, unless expressly described otherwise. Furthermore, the elements and/or features described regarding FIGS. 6A-B may be the same as and/or similar to other similarly named elements and/or features described and/or illustrated throughout this disclosure. System 600 includes housing 130, measurement device 110 and mobile device 120.

System 600 includes lancet 620 that is disposed in aperture 610 of housing 130. For example, aperture 610 is a void or space within housing 130. As such, lancet 620 is disposed within aperture 610. Lancet 620 is able to longitudinally translate with respect to aperture 610. Referring to FIG. 6A, lancet 620 is retracted within aperture 610. As such, lancet 620 is not accessible to the user and not able to lance the skin of a user.

Referring to FIG. 6B, lancet 620 is extended such that an end protrudes from housing 130. As such, lancet 620 is accessible to the user and able to lance the skin of a user. Upon lancing the skin, the lancet is able to be retracted into aperture 610 (as shown in FIG. 6A).

In one embodiment, lancet 620 may be replaced after one or more uses. For example, a user may remove lancet 620 from aperture 610 and dispose of the used lancet. The user may access another lancet, for example from cavity 410 or container 540 (see FIG. 5). The user may then provide the other lancet within aperture 610 to replace lancet 620.

In another embodiment, after lancing the skin of the user, lancet 620 may be sanitized and reused. In one example, lancet 620 may be further extended and a user may sanitize the lancet. The user may then use a wipe and/or spray bottle (accessed from cavity 410 or container 540) and sanitize the lancet. Upon sanitizing, lancet 620 is retracted into aperture 610 (as shown in FIG. 6A).

Figure 6C:
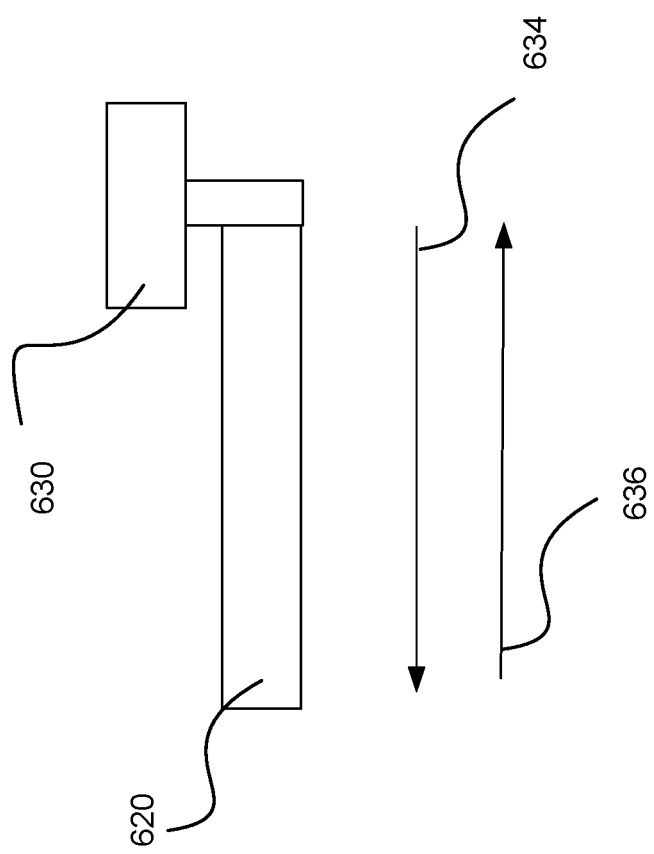
FIG. 6C illustrates a lancet, accordingly to an embodiment.

Lancet 620 may be extended/retracted by various means. For example, referring to FIG. 6C, lancet 620 is coupled to a feature 630 that may protrude from housing 130. A user may slide feature 630 in direction 634 to extend and slide feature 630 in direction 636 retract lancet 620, as described herein.

In another embodiment, lancet 620 is extended via a spring mechanism. For example, a spring coupled to lancet is compressed when lancet 620 is retracted. To extend lancet 620, the spring is released and extends to an uncompressed state. In doing so, the lancet extends (as shown in FIG. 6B).

Figure 7A:
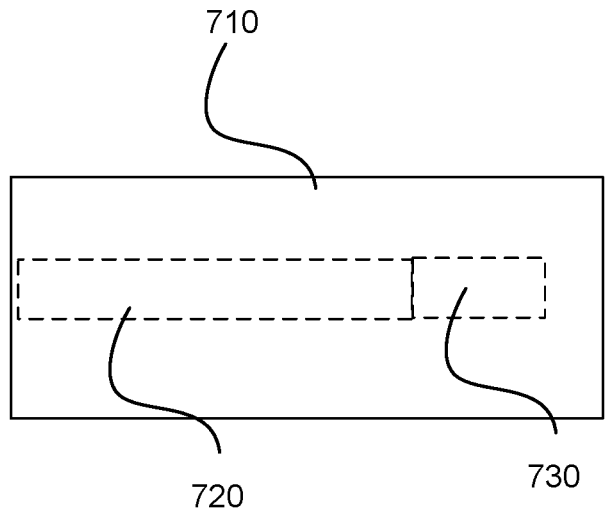
FIG. 7A illustrates a lancet system in a retracted position, accordingly to an embodiment.
Figure 7B:
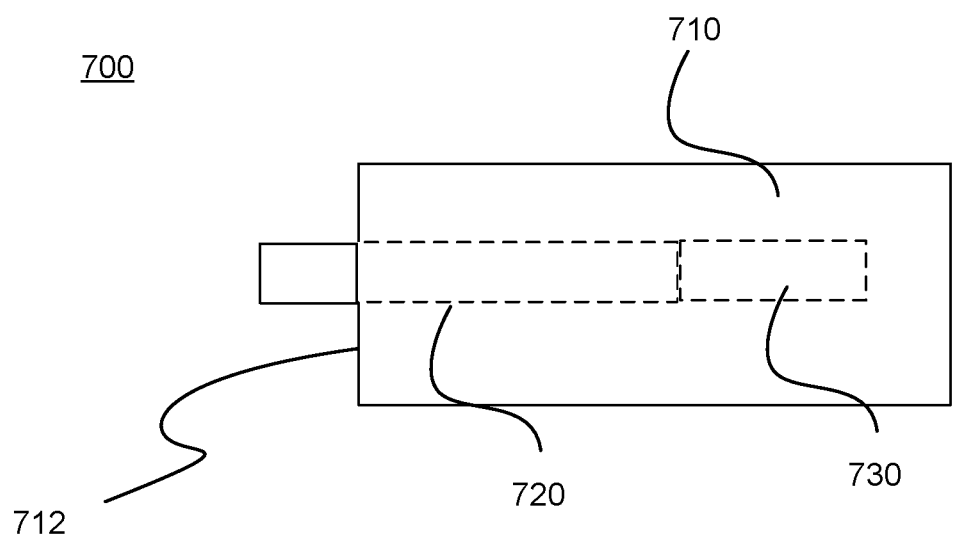
FIG. 7B illustrates a lancet system in an extended position, accordingly to an embodiment.
Figure 7C:
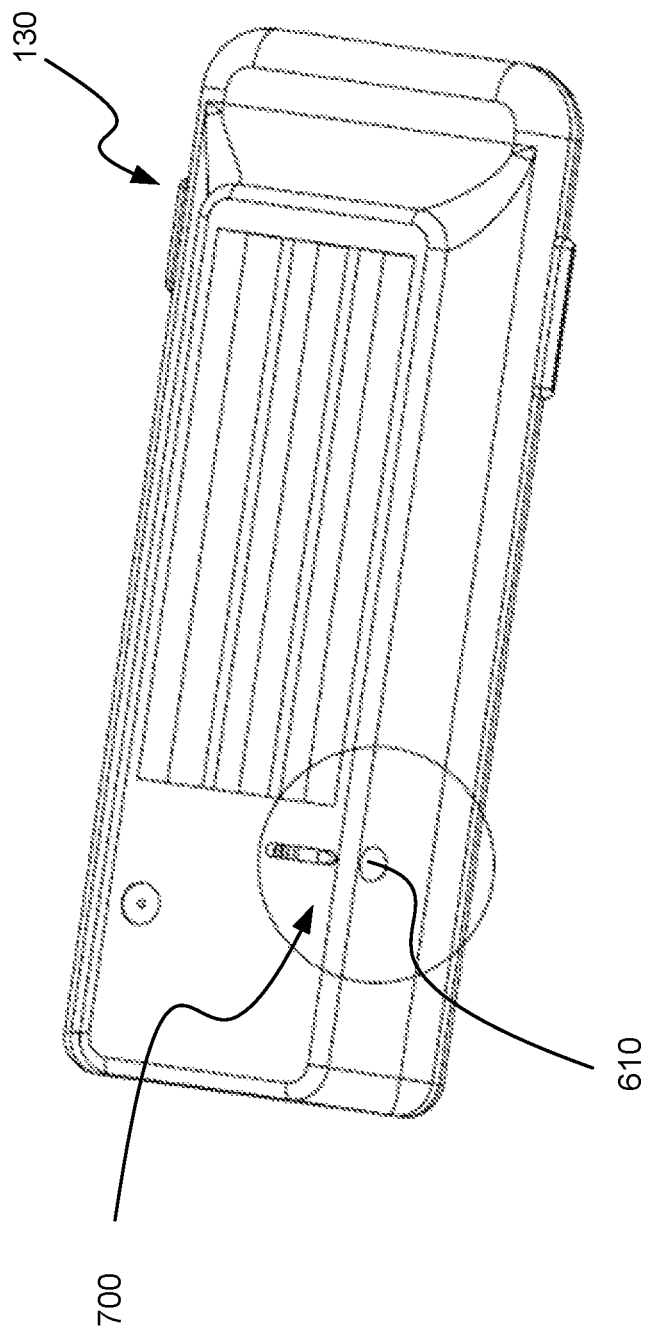
FIG. 7C illustrates a lancet system coupled to a housing, accordingly to an embodiment.

FIGS. 7A-C depict an embodiment of lancet system 700 used in conjunction with system 100. Lancet system 700 includes housing 710 where lancet 720 and spring 730 are disposed in housing 710.

FIG. 7A depicts lancet system 700 in a retracted position. As such, spring 730 is in a compressed state and lancet 720 is retracted within housing 710. As such, lancet 720 is not accessible to the user and not able to lance the skin of a user.

FIG. 7B depicts lancet system 700 in an extended position. As such, spring 730 is in an uncompressed state and lancet 720 is extended from housing 710. As such, lancet 720 is accessible to the user and able to lance the skin of a user. In one embodiment, a user places their finger at end 712 of housing 710. Upon release of spring 730, lancet 720 is thrust forward beyond end 712 and pierces the user's finger. Upon piercing the user's finger, the lancet is sanitized, as described herein, and retracted within housing 710 (as shown in FIG. 7A). Spring 730 may be released from the compressed position to the uncompressed position via a release mechanism.

FIG. 7C depicts lancet system 700 coupled to housing 130. Some of the features in FIG. 7C are the same as or similar to some of the features in FIGS. 1A-B, and FIGS. 3-6B as noted by same and/or similar reference characters, unless expressly described otherwise. Furthermore, the elements and/or features described regarding FIG. 7C may be the same as and/or similar to other similarly named elements and/or features described and/or illustrated throughout this disclosure. In particular, lancet system 700 is removably coupled to housing 130. For example, housing 710 is seated into housing 130, for example, in aperture 610 of housing 130. In one embodiment, the lancet system 700 may be removed from aperture 610 and replaced with another lancet system.

Figure 8:
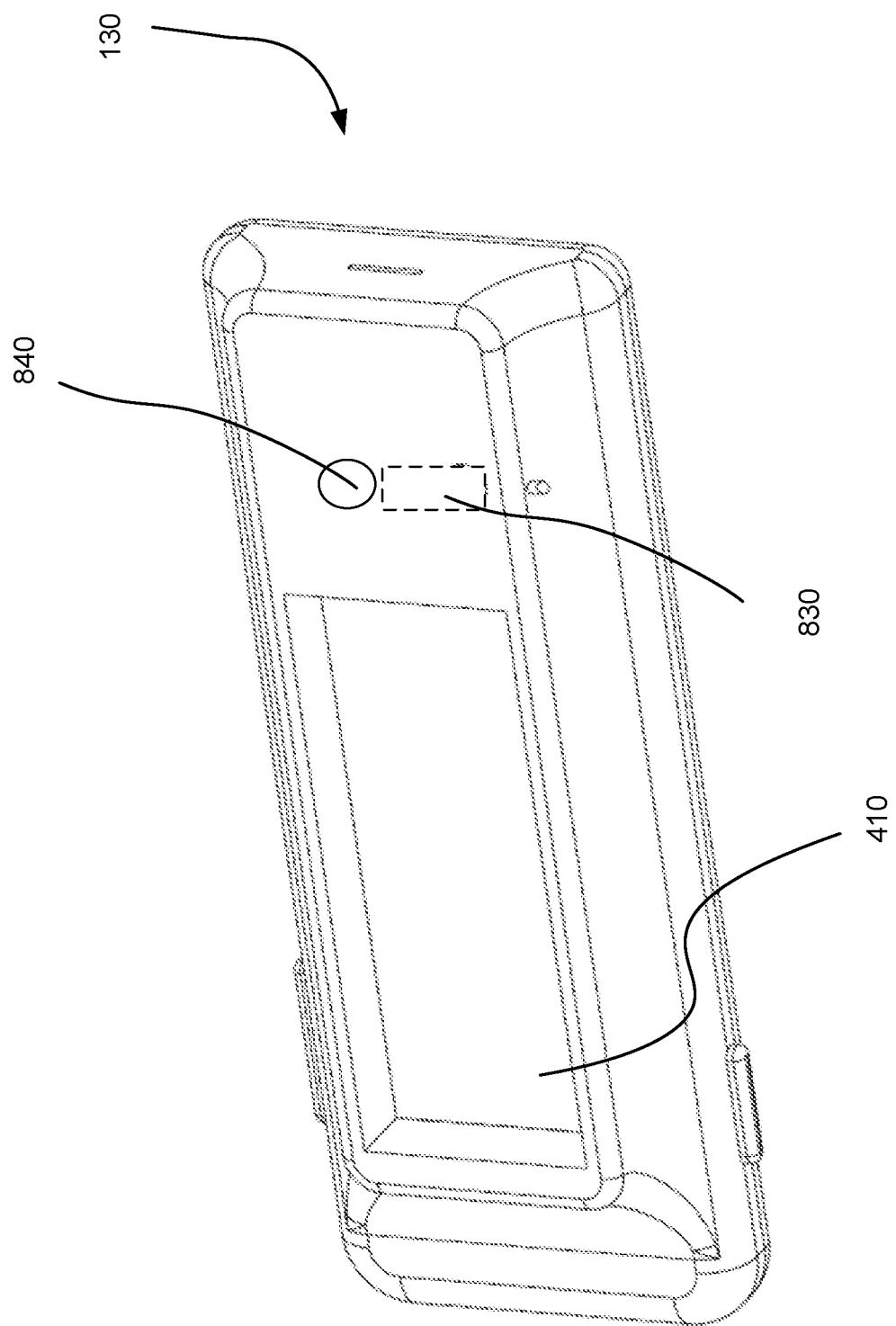
FIG. 8 illustrates a perspective back of view of a housing including a sanitizing component, accordingly to an embodiment.

FIG. 8 depicts an embodiment of system 800. System 800 is similar to at least system 100, 300, 400, 500 and/or 600 described herein. Some of the features in FIG. 8 are the same as or similar to some of the features in FIGS. 1A-B, FIGS. 3-6B and FIG. 7 as noted by same and/or similar reference characters, unless expressly described otherwise. Furthermore, the elements and/or features described regarding FIG. 8 may be the same as and/or similar to other similarly named elements and/or features described and/or illustrated throughout this disclosure. System 800 includes housing 130 and measurement device 110 and mobile device 120.

System 800 includes spray bottle 830 releasably coupled in (or to) housing 130. Spray bottle 830 may be releasably coupled to housing 130 via a latching mechanism, a press fit mechanism and so on. As such, spray bottle 830 may be replaced with another spray bottle when spray bottle 830 is empty.

Spray bottle 830, in one embodiment, includes a fluid (e.g., alcohol) to sanitize the skin of a user at a location to be pierced and/or pierced by a lancet. For example, spray bottle 830 is coupled to button 840. As such, when a user depresses button 840 fluid in the spray bottle 830 is spayed from spray bottle 830. In one embodiment, another spray bottle is stored in housing 130, such as in cavity 410. In various embodiments, when the contents of spray bottle 830 is depleted, the depleted spray bottle is removed (or ejected) from housing 130 and a replacement spray bottle is inserted into housing 130. The replacement spray bottle can be the same type of spray bottle as spray bottle 830 or a different type of spray bottle. Additionally, the replacement spray bottle may include the same type of sanitizer (e.g., an alcohol-based solution) or a different type of sanitizer (e.g., a non-alcohol based sanitizer).

Figure 9:
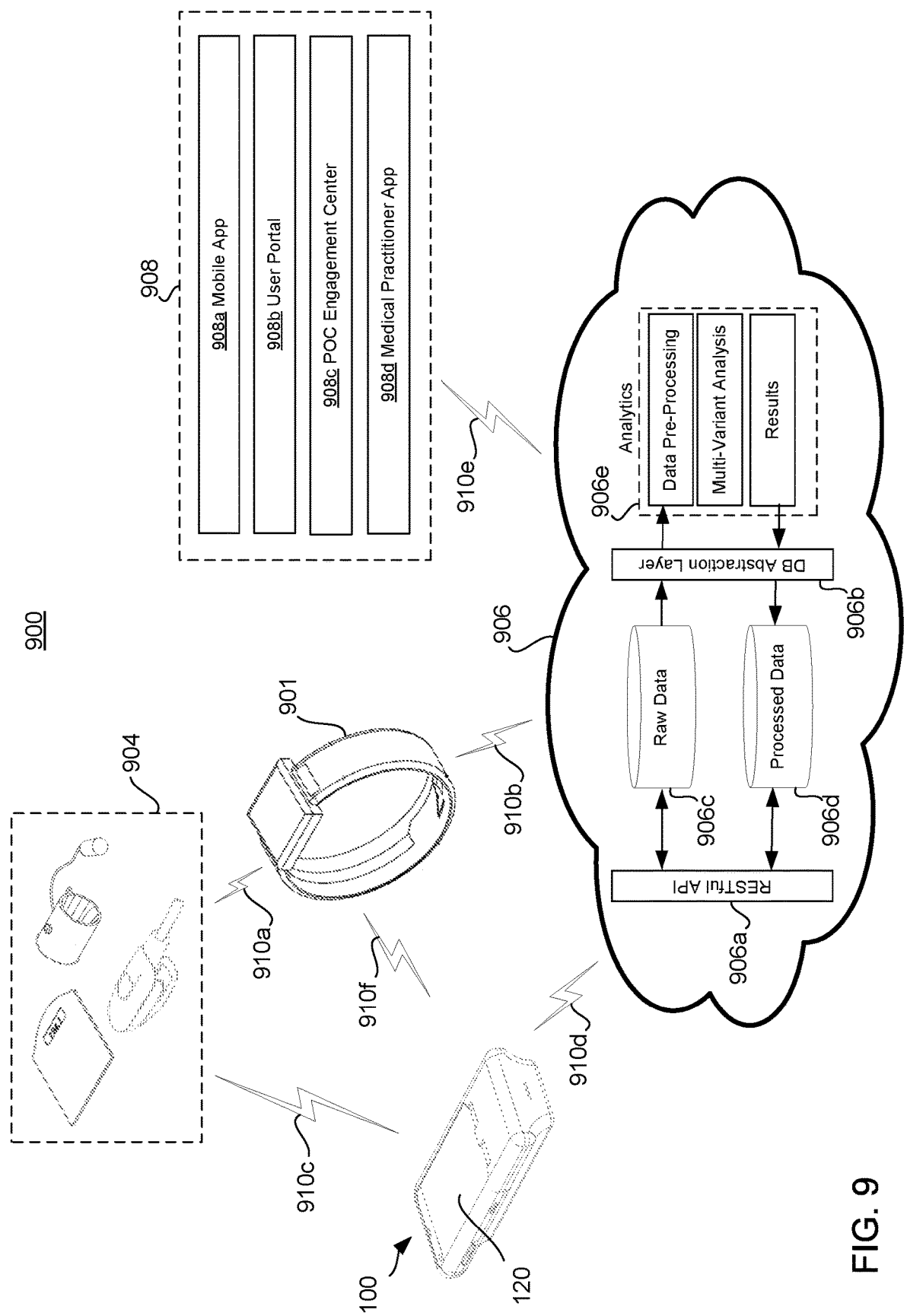
FIG. 9 illustrates a health device network configuration including a glucose monitoring system, according to an embodiment.

FIG. 9 illustrates a health device network configuration 900 for communicating health data, according to an embodiment. The health device network configuration 900 includes the wearable device 901, system 100, one or more peripheral measurement devices 904, a cloud-based server 906, and a user device 908. The wearable device 901 and the peripheral measurement devices 904 may communicate over a first network communication link 910a. The wearable device 901 and the cloud-based server 906 may communicate over a second network communication link 910b. Mobile device 120 of system 100 and the peripheral measurement devices 904 may communicate over a third network communication link 910c. Mobile device 120 and the cloud-based server 906 may communicate over a fourth network communication link 910d. The cloud-based server 906 and the user device 908 may communicate over a fifth network communication link 910e.

The health device network configuration 900 may include a body area network (BAN), a personal area network (PAN), a near-me area network (NAN), a local area network (LAN), a campus-area network (CAN), a metropolitan area network (MAN), a wide area network (WAN), an internet area network (IAN), and/or a public Internet network. The health device network configuration 900 may include two or more network types. For example, the health device network configuration 900 may include the PAN, the IAN, and the Internet. In another example, the health device network configuration 900 may include the BAN and the IAN. The health device network configuration 900 may include a point-to-point topology, a daisy chain topology, a bus topology, a star topology, a ring topology, and/or a mesh topology. The health device network configuration 900 may include a hybrid topology including two or more types of network topologies. For example, the health device network configuration 900 may include a mesh topology and a star topology. In another example, the health device network configuration 900 may include a point-to-point topology and a star topology.

As used throughout this disclosure, various terms may include a particular meaning. The term "campus" may refer to a group of rooms adjacent to each other in a building and/or a group of buildings adjacent to each other. The term "office" may refer to a single room within a building, a group of rooms within a building, or a building having one or more rooms. The term "hospital" may refer to a building and/or group of buildings dedicated to the provision of medical care, including in-patient and/or out-patient care. The term "home" may refer to a user and/or individual's residence. The term "metropolitan" may refer to a geographic region having homes, buildings, offices, and/or campuses. The term "remote" may refer to a device being accessible by another device via a network communication link. The term "remote" may also refer to non-adjacent locations. For example, two non-adjacent rooms within a building may be considered remote from each other, two non-adjacent buildings may be considered remote from each other, two non-adjacent metropolitan areas may be considered remote from each other, and so forth. The term "local" may refer to a device being connected via a closed and/or private network connection to another device. The term "local" may also indicate physical location within a same room, within a same building, on a same campus, and/or in a same metropolitan area, and so forth.

In various embodiments, the health device network configuration 900 may be situated in a single location, such as in a room, in a user's home, within an office building, and/or within a campus. For example, all networked elements of the health device network configuration 900 may be physically located in the same room as each other, in the user's home, within an office building, and/or on the same campus. In various other embodiments, the health device network configuration 900 may be situated across two or more locations, such as across two rooms, between a user's home and an office building, across buildings on different campuses from each other, across different metropolitan areas, and so forth. For example, some of the networked elements of the health device network configuration 900 may be situated in the user's home, and some of the networked elements may be situated in an office building housing a data center in a different city and/or country from the user's home. In another example, some of the networked elements may be situated in a medical office, some of the networked elements may be situated in a data center, and some of the networked elements may be mobile, accompanying the user as the user moves and travels from one location to another.

The network communication links 910*a-f* may be direct or indirect. A direct link may include a link between two devices where information is communicated from one device to the other without passing through an intermediary. For example, the direct link may include a Bluetooth™ connection, a Zigbee® connection, a Wifi Direct™ connection, a near-field communications (NFC) connection, an infrared connection, a wired universal serial bus (USB) connection, an ethernet cable connection, a fiberoptic connection, a firewire connection, a microwire connection, and so forth. In another example, the direct link may include a cable on a bus network. As used herein, "direct," when used regarding a network communication link, may refer to any of the aforementioned communication means of the direct link.

An indirect link may include a link between two or more devices where data may pass through an intermediary, such as a router, before being received by an intended recipient of the data. For example, the indirect link may include a wireless fidelity (WiFi) connection where data is passed through a WiFi router, a cellular network connection where data is passed through a cellular network router, a wired network connection where devices are interconnected through hubs and/or routers, and so forth. The cellular network connection may be implemented according to one or more cellular network standards, including the global system for mobile communications (GSM) standard, a code division multiple access (CDMA) standard such as the universal mobile telecommunications standard, an orthogonal frequency division multiple access (OFDMA) standard such as the long term evolution (LTE) standard, and so forth. As used herein, "indirect," when used regarding a network communication link, may refer to any of the aforementioned communication means of the indirect link.

The peripheral measurement devices 904 may include any of a variety of devices that may measure a physiological condition, physiological parameter, physiological constituent, and/or physiological element (collectively "physiological characteristic") of the user. Accordingly, the peripheral measurement devices 904 may include a weight scale, a blood pressure monitor, a pulse oximeter, a thermometer, a viscosity sensor, an ultrasound machine, a hygrometer, a pulsometer, an echocardiogram machine, an electrodermal activity device, a glucometer, an x-ray machine, and so forth. The peripheral measurement devices 904 may take the measurements by electronic means, mechanical means, chemical means, or combinations thereof, and so forth. The peripheral measurement devices 904 may therefore include electronics, structures, materials, reactants, and so forth, for taking the measurements. Furthermore, one or more of the peripheral measurement devices 904 may include electronics for processing and/or communicating the measurements. For example, one or more of the peripheral measurement devices 904 may include the processing component and/or the communication component.

A device of the one or more peripheral measurement devices 904 may be configured to communicate data generated and/or collected by the device to the user and/or to another device such as the wearable device 901, mobile device 120, and/or another of the peripheral measurement devices 904. The peripheral measurement devices 904 may be networked with the wearable device 901 and/or mobile device 120 in the BAN, the PAN, the NAN, or the LAN. The first network communication link 910*a* may include a direct link and/or an indirect link.

In an embodiment, the peripheral measurement devices 904, mobile device 120, and the wearable device 901 may be networked in a NAN. The NAN may include overlapping point-to-point topologies. The peripheral measurement devices 904 may include a weight scale, a blood pressure monitor, and a pulse oximeter. The peripheral measurement devices 904, mobile device 120, and the wearable device 901 may include hardware and software for Bluetooth™ communications. The peripheral measurement devices 904 may take a measurement from the user. The measurement may correspond to a physiological characteristic. For example, the weight scale may take a measurement corresponding to a weight of the user, the blood pressure monitor may take a measurement corresponding to a blood pressure of the user, and/or the pulse oximeter may take a measurement corresponding to a blood oxygen saturation of the user.

In an embodiment, the measurements may be communicated from the peripheral measurement devices 904 to the wearable device 901 over the first network communication link 910*a*. The first network communication link 910*a* may include a Bluetooth™ link. The measurements may be raw data. For example, the raw data may include one or more intensities of light detected by the pulse oximeter. In another example, the raw data may include pressure measurements and corresponding sonographic data detected by the blood pressure monitor. In yet another example, the raw data may include strain data from a load cell of the weight scale. The raw data may be processed by the wearable device 901. For example, a processing unit of the wearable device 901 may receive the wavelength data and may output a corresponding blood oxygen saturation. In another example, the processing unit may receive the pressure measurements and corresponding sonographic data and may output a corresponding blood pressure. In yet another example, the processing unit may receive the strain data and may output a corresponding weight. Wearable device 901 may display the blood oxygen saturation, the blood pressure, and/or the weight to the user. The processing unit may store the raw data and/or the corresponding physiological measurements.

In an embodiment, the peripheral measurement devices 904 may include processors that may process the raw data to output the corresponding physiological characteristics. The peripheral measure devices 904 may store the raw data and/or the corresponding physiological characteristics in local memory, such as in persistent and/or transitory memory in the processors. For example, the weight scale may store the strain measurements and/or the corresponding weights in a persistent memory of the weight scale. In another example, the pulse oximeter may store the wavelengths and/or the corresponding blood oxygen saturations in persistent a memory of the pulse oximeter. In yet another example, the blood pressure monitor may store the pressure measurements, the sonographic data, and/or the corresponding blood pressures in a persistent memory of the blood pressure monitor. The peripheral measurement devices 904 may communicate the physiological characteristics to the wearable device 901 over the Bluetooth™ link. The wearable device 901 may store the physiological characteristics and/or display the physiological characteristics to the user.

The wearable device 901 may correlate the raw data and/or the physiological characteristics from the peripheral measurement devices 904 with raw data and/or physiological characteristics measured by the wearable device 901. In an embodiment, the wearable device 901 may measure a hydration condition of the user and correlate the hydration condition to a weight of the user measured by the weight scale. Based on the correlation between the hydration condition and the weight, the wearable device 901 may determine a change in the weight of the user may be due to the user being dehydrated or to the user losing fat. The determination may be communicated to the user via the display of device 901. In another embodiment, the wearable device 901 may determine a blood glucose level of the user and correlate the blood glucose level of the user with a blood pressure of the user. The wearable device 901 may determine that an increase in the blood pressure of the user corresponds to a subsequent sharp increase in the blood glucose level of the user. The wearable device 901 may determine based on the correlation that the user eats when the user experiences stress. The determination may be communicated to the user via the display.

The raw data and/or the physiological characteristics measured by the peripheral measurement devices 904 may be communicated to mobile device 120 over the third network communication link 910c. The third network communication link 910c may include a Bluetooth™ link. Mobile device 120 may receive the raw data. The processing component of mobile device 120 may process the raw data and output the corresponding physiological characteristic. Mobile device 120 may display the physiological characteristic to the user. In an embodiment, mobile device 120 may process the raw data and output the corresponding physiological characteristics. The peripheral measurement devices 904 may store the raw data and/or the physiological characteristics in persistent and/or transient memory. The raw data and/or the physiological characteristics may be communicated mobile device 120. Mobile device 120 may store the raw data and/or the physiological characteristics. Mobile device 120 may display the physiological characteristics to the user.

Mobile device 120 may correlate the raw data and/or the physiological characteristics from the peripheral measurement devices 904 with raw data and/or physiological characteristics measured by the wearable device. In an embodiment, measurement device 110 may determine a blood glucose level of the user and mobile device 120 may correlate the blood glucose level of the user with a blood pressure of the user measured by the blood pressure monitor. Mobile device 120 may determine that a sharp decrease in the blood pressure of the user follows a sharp increase in the blood glucose level of the user. Mobile device 120 may determine based on the correlation that the user is experiencing a hyperglycemic event. The determination may be communicated to the user via the user interface, along with a recommendation of how to resolve the hyperglycemic event, such as by recommending the user take a shot of insulin. In another embodiment, mobile device 120 may correlate the blood glucose level of the user with a blood oxygen saturation of the user measured by the pulse oximeter. The correlation may be communicated to a remote server such as the cloud-based server 906 for comparison with a blood glucose measurement taken by the wearable device 901. The cloud-based server 906 may compare the two blood glucose measurements and the blood oxygen saturation measurement to determine a component of the measurement taken by the wearable device 901 which may be attributable to blood oxygen.

The cloud-based server 906 may include a physical and/or virtual server. For example, the cloud-based server 906 may include one or more bare-metal servers. The bare-metal servers may be single-tenant servers or multiple tenant servers. In another example, the cloud-based server 906 may include a bare metal server partitioned into two or more virtual servers. The virtual servers may include separate operating systems and/or applications from each other. In yet another example, the cloud-based server 906 may include a virtual server distributed on a cluster of networked physical servers. The virtual servers may include an operating system and/or one or more applications installed on the virtual server and distributed across the cluster of networked physical servers. In yet another embodiment, the cloud-based server 906 may include more than one virtual server distributed across the cluster of networked physical servers.

The cloud-based server 906 may include a processing component and a communication component. The processing component may include a processing device and a memory device. One or more applications may be stored in the memory device and/or executed by the processing device. For example, one or more application programming interfaces (APIs) may be installed on and/or executed by the cloud-based server 906. In another example, one or more database applications may be installed on and/or executed by the cloud-based server. In yet another example, one or more data analytics applications may be installed on and/or executed by the cloud-based server. The communication component may include hardware and/or software enabling the cloud-based server 906 to communicate with other devices. The hardware may include one or more antennas and/or hardwire communication ports. The software may include programming which, when executed, may generate signals which may be communicated from the cloud-based server via the antennas and/or hardwire communication ports. In one embodiment, the cloud-based server 906 may communicate wirelessly via Wifi and/or over hardwire via one or more ethernet cables. In various embodiments, software, APIs, and/or applications run on and/or installed on the cloud-based server 906 may be hidden from other devices networked to the cloud-based server 906.

In an embodiment, the APIs may include a representational state transfer (RESTful) API configuration 906a. The RESTful API 906a may enable data calls to the cloud-based server 906 from a variety of devices and/or applications having different hardware and/or software architectures. The APIs may further include a database abstraction layer 906b. The database applications may include a raw data database 906c and a processed data database 906d. The cloud-based server 906 may include a data analytics application 906e.

The data analytics application 906e may include, for example, a data pre-processing component, a multi-variant analysis component, and a results component. The data analytics application 906e may generate a predictive model, may identify correlations between data, may integrate measurement data from two or more measurement devices, and so forth. In an embodiment, the predictive model may correlate invasive glucose measurements to non-invasive glucose measurements to identify one or more trends in the invasive glucose measurements and/or the non-invasive glucose measurements.

In an embodiment, the RESTful API 906a may convert data communicated to the cloud-based server 906 from a format corresponding to a device from which the data was communicated into a format in which the data may be stored on and/or processed by the cloud-based server 906. The communicated data may be stored in the raw data database 906c. The data analytics application 906e may request the communicated data. The communicated data may be passed to the database abstraction layer 906b. The database abstraction layer 906b may convert the communicated data into a format that may be read and/or manipulated by the data analytics application 906e. The data analytics application 906e may process the communicated data and output resulting data. The resulting data may be passed to the processed data database 906d. The database abstraction layer 906b may convert the resulting data to a format in which the data may be stored in the processed data database 906d. The resulting data may be converted by the RESTful API 906a to a format corresponding to another device. The other device may request the resulting data and/or the cloud-based server 906 may include instructions to communicate the resulting data. For example, the cloud-based server 906 may include instructions to communicate the resulting data to the other device automatically once the resulting data has been output by the data analytics application 906e.

In another embodiment, processed data may be communicated to the cloud-based server 906. The processed data may be converted by the RESTful API 906a and stored in the processed data database 906d. The processed data may be communicated from the cloud-based server 906 to the other device. The processed data may be requested by the other device, and/or the cloud-based server 906 may store instructions to automatically communicate the data to the other device. In yet another embodiment, raw data stored in the cloud-based server 906 may be communicated to the other device. The other device may request the raw data, and/or the cloud-based server 906 may store instructions to automatically communicate the raw data to the other device.

The cloud-based server 906 may be physically located near the wearable device 901, system 100, and/or the peripheral measurement devices 904. For example, the cloud-based server 906 may be located in the same room, in the same building, and/or on the same campus as the wearable device 901, system 100, and/or the peripheral measurement devices 904. In an embodiment, the cloud-based server 906, the wearable device 901, system 100, and/or the peripheral measurement devices 904 may be located on a health care campus. In another embodiment, the cloud-based server 906, the wearable device 901, system 100 and/or the peripheral measurement devices 904 may be located in a hospital.

The cloud-based server 906 may be physically located remotely from the wearable device 901, system 100, and/or the peripheral measurement devices 904. For example, the cloud-based server 906 may be located in a different building, on a different campus, in a different metropolitan area, in a different country, and/or on a different continent as the wearable device 901, system 100, and/or the peripheral measurement devices 904. In another example, the cloud-based server may be located in a data center. In yet another example, the cloud-based server 906 may be distributed across two or more locations remote from each other and located remotely from the wearable device 901, system 100, and/or the peripheral measurement devices 904. In an embodiment, the wearable device 901, system 100, and/or the peripheral measurement devices 904 may be located at the user's home and the cloud-based server 906 may be located in a different city than the user's home. In another embodiment, the wearable device 901, the system 100, and/or the peripheral measurement devices 904 may be located in a medical office and the cloud-based server 906 may be located in a different building complex than the medical office.

The cloud-based server 906, the wearable device 901, system 100, and/or the peripheral measurement devices 904 may be configured together in or more network topologies. For example, the network may include a ring-type topology, a star topology, and/or a tree topology. In an embodiment where the network is configured in a ring-type topology, data may pass freely back and forth between one of the peripheral measurement devices 904 and the wearable device 901, data may pass freely back and forth between the peripheral measurement device and system 100, data may pass freely back and forth between the cloud-based server 906 and the wearable device 901, and data may pass freely back and forth between the cloud-based server 906. Data may not pass between the wearable device 901 and mobile device 120 through the peripheral measurement device. In an embodiment where the network is configured in a tree topology, data may flow from the peripheral measurement devices 904 through the wearable device 901 to the cloud-based server 906, and from mobile device 120 to the cloud-based server 906.

In embodiments where the cloud-based server 906, the wearable device 901, system 100 and/or the peripheral measurement devices 904 may be physically located near each other, the network may include a NAN, a LAN, and/or a CAN. In some embodiments where the cloud-based server 906, the wearable device 901, system 100, and/or the peripheral measurement devices 904 may be physically located near each other, the network may include a MAN, a WAN, an IAN, and/or the Internet. In embodiments where the cloud-based server 906 may be located remotely from the wearable device 901, system 100, and/or the peripheral measurement devices 904, the network may include a MAN, a WAN, an IAN, and/or the Internet. The wearable device 901, system 100, and/or the peripheral measurement devices 904 may be networked together in a BAN, PAN, NAN, LAN, and/or CAN, and the cloud-based server 906 may be networked together with the wearable device 901 and/or the system 100 in a MAN, a WAN, an IAN, and/or over the Internet.

Measurement data such as the raw data and/or the physiological characteristics collected, processed, and/or output by the peripheral measurement devices 904 and/or the wearable device 901 may be communicated to the cloud-based server 906 over the second network communication link 910b. Measurement data such as the raw data and/or the physiological characteristics collected, processed, and/or output by the peripheral measurement devices 904 and/or system 100 may be communicated to the cloud-based server 906 over the fourth network communication link 910d. The second network communication link 910b and/or the fourth network communication link 910d may include a direct link and/or an indirect link. For example, the second network communication link 910b and/or the fourth network communication link 910d may include a Bluetooth™ connection, a Wifi connection, a USB connection, an ethernet connection, a cellular network connection, and/or generally an Internet connection.

The user device 908 may include a processing component, a communication component, and/or a user interface. The processing component may include a processing device and/or a memory device. The communication component may include hardware and/or software which may be configured to communicate data with another device, such as the cloud-based server 906, another user device, system 100, the wearable device 901, the peripheral measurement devices 904, and so forth. The user interface may include a screen, buttons, a microphone, a speaker, and/or a touchscreen. The user interface may communicate information to the user, such as by displaying information or playing sounds, and/or may receive input from the user. In various embodiments, the user device 908 may include a personal computer, a mobile device such as a mobile phone, a personal digital assistant, a tablet computer, an artificial intelligence telephony system, an interactive voice recognition system, and so forth.

The user device 908 may include an application that may communicate health information with the user. The health information may be health information of a patient. The user may include the patient, a health care provider such as a nurse, doctor, and/or physician's assistant, a health care insurer, a third party authorized by the patient to access the patient's health information such as an individual with power of attorney for the patient, a healthcare partner of the patient, and so forth. In an example, the healthcare partner may include a third party who reviews the patient's healthcare information and communicates with the patient about the patient's health. The healthcare partner may include an employee of a healthcare customer service center such as a call center.

The health information application may be tailored to provide specific information for a specific user. The user may interface with the application via the user device 908. The health information application may enable the user device 908 to display the health information to the user, and/or the health information application may enable the user to input the health information into the user device 908, such as via the user interface. The health information application may include software which may cause the processor to render an output based on an input. The software may provide instructions for rendering the output based on the input. The health information application may be installed on the user device 908 and/or the application may be installed on a device physically remote from the user device 908. For example, the application may be installed on a server and may be accessed via a network from the user device 908 by a web browser installed on the user device. In various embodiments, the application may include a mobile application 908a, a user portal 908b, a point-of-care (POC) engagement center application 908c, and/or a medical practitioner application 908d.

The health information application may be tailored to provide specific information which may depend on the type of device through which the health information may be communicated. The device type may include features such as how information is provided to the user and how information is input into the device by the user and/or another device. The tailoring may be the same for different devices, or the tailoring may be different for different devices. For example, information displayed on a mobile device such as a mobile phone and/or tablet may be different than information displayed on a personal computer. Information displayed on a mobile phone may be different than information displayed on a tablet. In an embodiment, information displayed by the personal computer may include detailed historical information about the patient, such as past medical charts, names of providers, dynamic graphs of physiological characteristics, live vitals, current and past diagnoses, detailed demographic data, and so forth. Information displayed by the mobile device may include current vitals, goals and tracking of progress towards those goals, upcoming appointments, messages, and so forth.

The format and/or programming of the application may correspond to the device type, or the format and/or programming of the application may be independent of the device type. For example, the application may be formatted to be installed on a mobile device, the application may be formatted to be installed on a server such as a local server and/or a web server, the application may be formatted to be installed on a personal computer, and so forth. The application may be formatted to be displayed by a web browser and may dynamically change the type and/or format of the information displayed based on whether the web browser is operating on a personal computer, a virtual computer, a mobile device, and so forth. In an embodiment, the application may allow the user to choose how and/or what type of information is displayed to the user without regard to the type of device and/or the format of the application.

The health information application may be tailored to provide specific information which may correspond to the format and/or programming of the application. The tailoring may be the same for different application types, or the tailoring may be different for different application types. For example, health information about the patient provided via the mobile application 908a may be different than health information about the patient provided via the user portal 908b, the POC engagement center application 908c, and/or the medical practitioner application 908d. Health information about the patient provided via the user portal 908b may be different than health information about the patient provided through the mobile application 908a, the POC engagement center application 908c, and/or the medical practitioner application 908d. Health information about the patient provided via the POC engagement center application 908c may be different than health information about the patient provided via the mobile application 908a, the user portal 908b, and/or the medical practitioner application 908d. Health information about the patient provided via the medical practitioner application 908d may be different than health information about the patient provided via the mobile application 908a, the user portal 908b, and/or the POC engagement center application 908c.

In an embodiment, input accepted via the application may be tailored based on the device type, the format and/or programming of the application, and/or the user. For example, the application may display the patient's medical chart to the patient via the user portal 908b and the user portal 908a may prevent the patient from editing the medical chart information. Continuing the example, the application may display the patient's medical chart to a healthcare provider via the mobile application 908a and the mobile application 908a may accept input from the healthcare provider which may add information to the patient's medical chart and/or change information in the patient's medical chart. In another example, the application may display health goals of the patient to the patient via mobile application 908*a* and may accept input from the patient via the mobile application 908*a* such as adding new goals and/or recording progress towards the goals, and so forth. Continuing the example, the application may display the patient's goals and/or progress towards the goals to a third party such as a family member of the patient via the mobile application 908*a*. The mobile application 908*a* may prevent the family member from editing the goals and/or adding progress to the goals.

The fifth network communication link 910*e* may enable and/or facilitate transmission of data between the cloud-based server 906 and the user device 908. The fifth network communication link 910*e* may be part of a LAN, CAN, MAN, WAN, IAN, and/or the internet. In various embodiments, the fifth network communication link 910*e* may include two or more forms of signal transmission and/or one or more intermediary devices. For example, the fifth network communication link 910*e* may include a hardlines, a network router, and/or a network switch between the cloud-based server 906 and a cellular network switch. The fifth network communication link 910*e* may further include a hardline between the cellular network switch and a cellular tower. The fifth network communication link 910*e* may further include a wireless link between the cellular tower and the user device 908. In another example, the fifth network communication link 910*e* may include a hardline connected to the cloud-based server 906 and a network switch, and a hardline connected to the network switch and the user device 908.

In various embodiments, the fifth network communication link 910*e* may include a direct link between the user device 908 and the cloud-based server 906. For example, the cloud-based server 906 and the user device 908 may be part of a LAN, and the cloud-based server 906 may be networked to the internet. The cloud-based server 906 may include a virtual server installed on a bare-metal server. The bare metal server may be located in an office with the user device 908. The user device 908 may be connected to the bare metal server by a hardline connection such as an ethernet cable. The bare metal server may be connected to the internet wirelessly and/or via a hardline connection.

The elements of the health device network configuration 900, including the devices, the server, and the network communication links, may form an independent and/or isolated network. The independent and/or isolated network may include a LAN, CAN, MAN, IAN, and/or WAN. The health device network configuration 900 may be physically isolated from devices outside the health device network configuration 900. For example, wireless and/or hardline connections may be limited to in-network devices. The health device network configuration 900 may be virtually isolated from devices outside the health device network configuration 900. For example, wireless and/or hardline connections may extend to out-of-network devices, but communication with in-network devices by out-of-network devices may be restricted by a firewall, a paywall, network authentication, encryption, and so forth.

Within the health device network configuration 900, devices may communicate in one or more of a variety of ways. In one embodiment, measurement data may be passed from one or more of the peripheral measurement devices 904 to the wearable device 901 over the first network communication link 910*a*. The wearable device 901 may combine the measurement data from the peripheral device with measurement data collected from the user by the wearable device 901, such as by a first sensor and/or the second sensor. The combined measurement data may be communicated to the cloud-based server 906 over the second network communication link 910*b* and stored in the raw data database 906*c*. The raw combined measurement data may be processed by the data analytics application 906*e* and stored in the processed data database 906*d*. The user may request the processed combined measurement data through the mobile application 908*a* installed on the user device 908, which may include a mobile phone. The processed combined measurement data may be transmitted to the mobile phone over the fifth network communication link 910*e* and/or may be displayed to the user via the mobile application 908*a*.

In another embodiment, measurement data may be passed from one or more of the peripheral measurement devices 904 to the system 100 over the third network communication link 910*c*. The user may input instructions into the system 100 that the measurement data is to be processed by the cloud-based server 906. The instructions may include instructions to push a notification to the user device 908, which may include a personal computer, that the measurement data is available for access by the user device 908. The measurement data may be transmitted to the cloud-based server 906 over the fourth network communication link 910*d*. The cloud-based server 906 may store and/or process the measurement data. The cloud-based server 906 may transmit the notification to the user device 908 over the fifth network communication link 910*e*. The notification may be communicated to a user of the personal computer through the user portal 908*b*. The user of the personal computer may request the measurement data in raw and/or processed form through the user portal 908*b*. The cloud-based server 906 may transmit the measurement data to the personal computer over the fifth network communication link 910*e*. The user of the personal computer may view and/or manipulate the measurement data through the user portal 908*b*.

In yet another embodiment, the wearable device 901 and the system 100 may take separate measurements contemporaneously, where "contemporaneous" refers to measurements taken simultaneously and/or within a time period of each other, the time period less than a time period of change for a respective analyte. For example, the analyte may be glucose and "contemporaneous" may refer to measurements taken within 1-5 minutes of each other. The measurement by the wearable device 901 may be communicated to the cloud-based server 906 over the second network communication link 910*b*. The wearable device 901 measurement may include a series of continuous, time-indexed blood glucose measurements. The measurement by the system 100 may be communicated to the cloud-based server 906 over the fourth network communication link 910*d*. The invasive analyte measurement may include a time-indexed blood glucose measurement. The data analytics application 906*e* may correlate the time-indexed invasive blood glucose measurement with at least one of the series of continuous, time-indexed blood glucose measurements from the wearable device 901. The correlation may include a time correlation, where the two measurements have the same time index. The cloud-based server 906 may communicate the correlation to the wearable device over the second network communication link 910*b*. The cloud-based server 906 may communicate the correlation to the system 100 over the fourth network communication link 910*d*. The cloud-based server 906 may communicate the correlation to the user device 908 over the fifth network communication link 910*e*.

The wearable device 901, an invasive analyte measurement device (e.g., measurement device 110 of system 100), the peripheral measurement devices 904, the cloud-based server 906, and/or the user device 908 may be physically located near each other. For example, the user device 908, the wearable device 901, the invasive analyte measurement device, the peripheral measurement devices 904, and/or the cloud-based server 906 may be located in the same room, in the same building, and/or on the same campus. In an embodiment, the user device 908, the wearable device 901, the system 100, the peripheral measurement devices 904, and/or the cloud-based server 906 may be located on the same health care campus. In another embodiment, the user device 908, the wearable device 901, the system 100, the peripheral measurement devices 904, and/or the cloud-based server 906 may be located in the same hospital.

The user device 908, the cloud-based server 906 the wearable device 901, the invasive analyte measurement device, and/or the peripheral measurement devices 904 may be physically located remotely from each other. For example, the user device 908, the cloud-based server 906, the wearable device 901, the system 100, and/or the peripheral measurement devices 904 may be located in a different building, on a different campus, in a different metropolitan area, in a different country, and/or on a different continent from each other. In an embodiment, the wearable device 901, the invasive analyte measurement device, and/or peripheral measurement devices 904 may be located at the user's home, the cloud-based server 906 may be located in a different city than the user's home, and the user device 908 may be located in a different city than the cloud-based server 906 and/or in a different city than the user's home. For example, the cloud-based server 906 may be physically located in a data center and the user device 908 may be located in a call center. In another embodiment, the peripheral measurement devices 904 may be located in a medical office and the wearable device 901 may be worn by the user and may accompany the user as the user travels from one location to another. The user may carry the system 100 with the user, may leave the system 100 at the user's home, and so forth. The cloud-based server 906 may be located in a data center and the user device 908 may be located in a call center.

Figure 10:
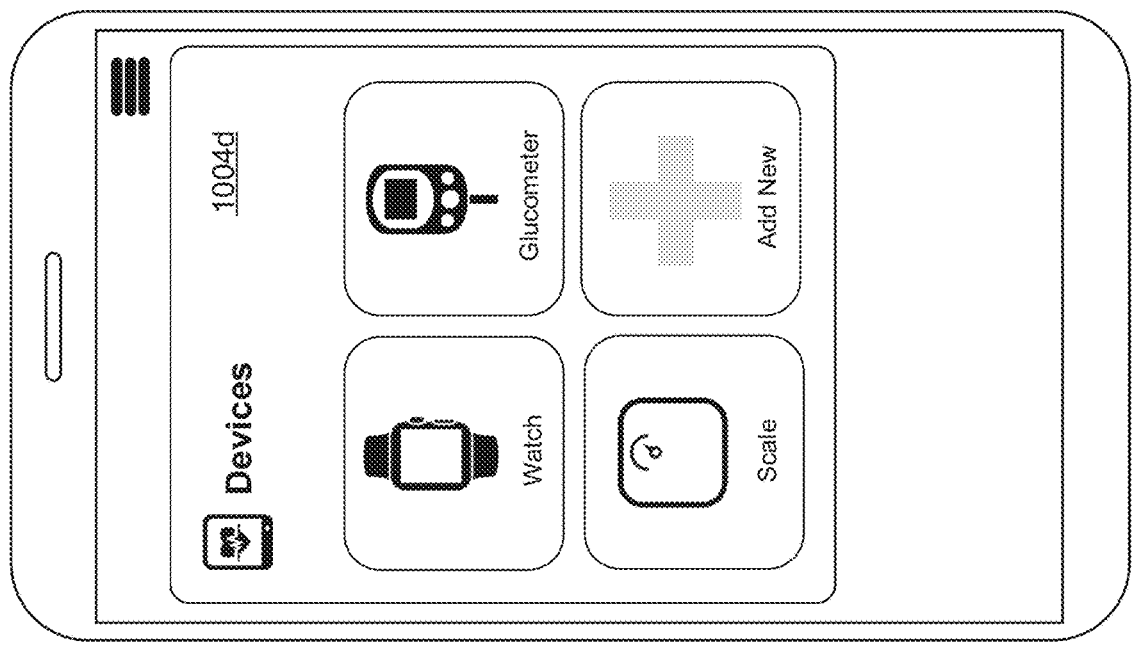
FIG. 10 illustrates a mobile device executing a mobile application, according to an embodiment.
Figure 10:
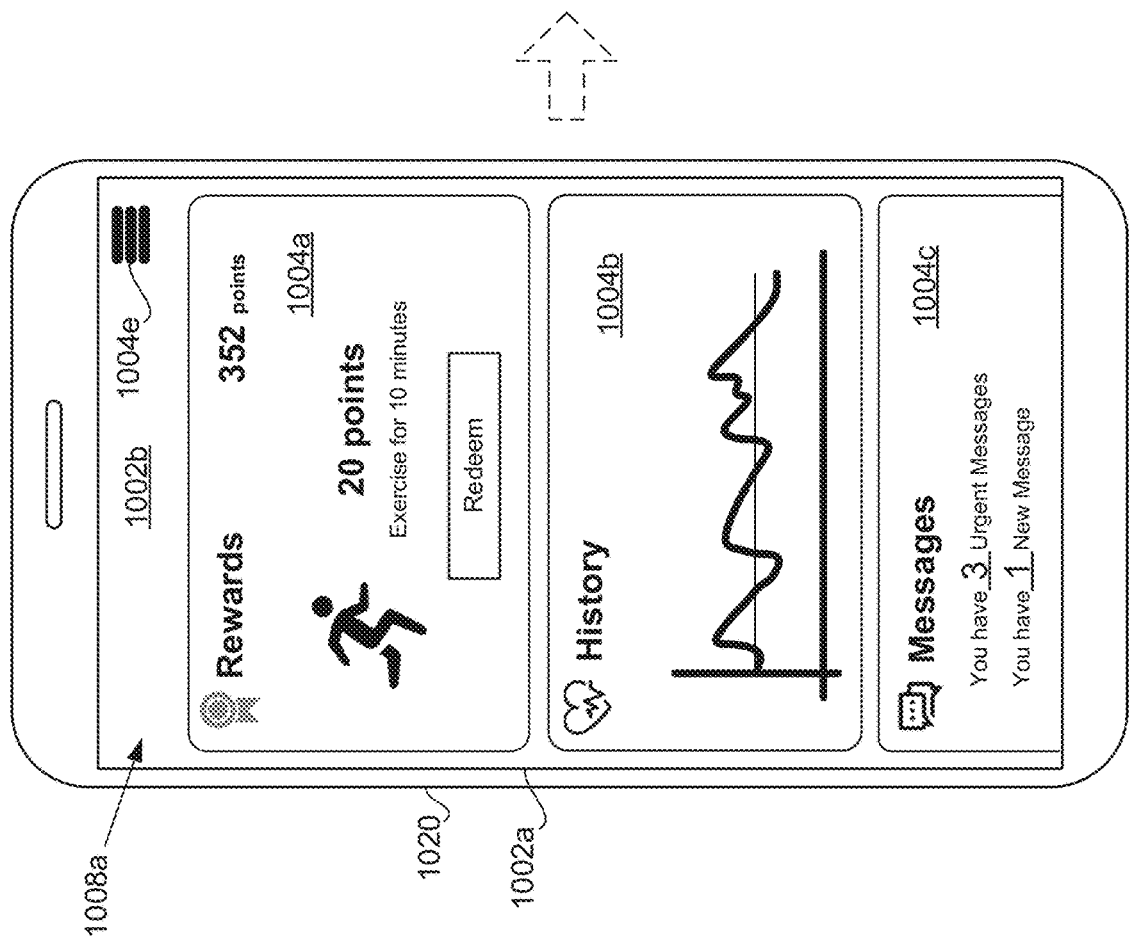

FIG. 10 illustrates mobile device 1020 (e.g., user device 908 and/or mobile device 120 of system 100) running a mobile application (e.g., mobile application 908a), according to an embodiment. Mobile device 1020 may include a touchscreen 1002a displaying a GUI 1002b. Via the GUI 1002b, the mobile application 1008a may display information to the user and may accept input from the user. The information may be displayed to the user via one or more modules. The modules may, in an embodiment, include a rewards module 1004a, a history module 1004b, a messages module 1004c, a devices module 1004d, and/or a menu module 1004e. Various other embodiments may include these and/or other modules, including an appointment module, a share module, a healthcare provider finder module, and so forth.

In one embodiment, the mobile application 1008a may be tailored for the patient, the third party, a non-medical user, and so forth. The tailoring may be the same for different users, or the tailoring may be different for different users. For example, a first instance of the mobile application 1008a may be tailored for use by the patient and a second instance of the mobile application 1008a may be tailored for use by a healthcare provider such as a nurse, doctor, practice manager, and so forth. In another example, a first instance of the mobile application 1008a may be tailored for use by the patient and a second instance of the mobile application 1008a may be tailored for use by a third party. The third party may, for example, be a friend of the patient, a family member of the patient, or a care provider of the patient. The first instance of the mobile application 1008a may display detailed personal information about the patient such as the patient's demographic information, the patient's vitals, the patient's goals and/or progress towards those goals, the patient's medications, the patient's medical history, information about the patient's medical provider, information about the patient's medical insurer, and so forth. The second instance of the mobile application 1008a may display limited information about the patient. For example, the second instance of the mobile application 1008a may display some of the patient's live vitals such as the patient's heart rate, the patient's electrocardiograph, the patient's glucose levels, the patient's hydration level, and so forth. The second instance of the mobile application 1008a may display the patient's goals and/or progress towards those goals. In one embodiment, the patient may select via the first instance of the mobile application 1008a what information is visible via the second instance of the application 1008a, up to and including all information available to the patient via the first instance of the mobile application 1008a.

The modules may include programming for receiving inputs from the user via the GUI 1002b and/or programming for generating outputs. The outputs may be displayed to the user via the GUI 1002b, stored in memory of the user device 908 (and/or mobile device 120), and/or sent from the user device 908 (and/or mobile device 120) to another device such as the cloud-based server 906. The outputs may correspond to the inputs received from the user and/or the outputs may correspond to data received by the user device 908 (and/or mobile device 120) from another device such as the cloud-based server 906. For example, the user may input information into one of the modules via the GUI 1002b. The module may cause the information to be stored in the memory of the user device 908 (and/or mobile device 120). The module may additionally and/or alternatively cause the information to be communicated to another device such as the cloud-based server 906. The module may additionally and/or alternatively cause the information to be displayed to the user. In another example, the user device 908 (and/or mobile device 120) may receive information from another device such as the cloud-based server. The programming of the module may cause the information to be stored in the memory of the user device. The programming of the module may cause the information to be displayed via the GUI 1002b to the user. The information may prompt an input from the user.

The rewards module 1004a may record the user's goals and/or track the user's progress towards the goals. The goals may be health-related goals. For example, the goals may include an exercise goal, a sleep goal, a blood glucose goal, a stress level goal, and so forth. The exercise goal may include exercising for a certain amount of time, exercising a certain number of times, having a heart rate over a certain level, and so forth. The sleep goal may include sleeping for a certain amount of time, achieving a certain amount of rapid eye movement (REM) sleep, and so forth. The blood glucose goal may include decreasing the user's fasting hemoglobin A1c (A1c) level, decreasing a range of variation of the user's blood glucose level, and so forth. The stress level goal may include decreasing the user's average resting heart rate, decreasing the user's average resting blood pressure, and so forth. The rewards module 1004a may include programming for awarding one or more rewards as the user records progress towards the user's goals. The rewards may include points. The points may be added as the user progresses towards the goals and/or may be removed as the user digresses from the goals. In an embodiment, the user may redeem the points, such as for a gift card, a rebate, a prize, and so forth.

The history module 1004b may include programming to store and/or display past and/or present data regarding one or more physiological characteristics of the user. The past and/or present data may include a graph, a table, a list, a current value, a past value, a maximum value, a minimum value, an average value, an optimal value, and so forth. For example, the past and/or present data may include a graph of physiological characteristic measurements indexed to a time stamp and/or indexed over a time interval. The physiological characteristics may include a heart rate, a blood pressure, a hydration condition, a blood glucose level, and so forth. The blood glucose level may include a distinction between an invasively measured blood glucose level and a non-invasively measured blood glucose level. In one embodiment, the history module 1004b may be programmed to display a graph showing continuous blood glucose measurements taken non-invasively from the user. The blood glucose measurements may be taken by the wearable device and communicated to the user device 908 (and/or mobile device 120) via the cloud-based server 906.

The messages module 1004c may include programming to display a message, a message notification, a message drafting interface, and so forth. The message may include a message from another user of another instance of the user device 908 application. For example, the message may be from a customer service agent using the POC engagement center application 908c. The message may be from a health care provider using the medical practitioner application 908d, and so forth. The message may be an automated message sent by an entity such as a healthcare provider company, a health insurance company, and so forth. The message notification may include a new message notification, an unread message notification, and so forth. The messages module 1004c may include programming to receive input from the user and/or generate a message based on the user input. The message may be sent via the mobile application 908a to another instance of the user device 908 application. The message may include an email message, a text message, an internet message, and so forth. The message drafting interface may accept the user input to generate the message based on the user input.

The devices module 1004d may include a list of one or more measurement devices which may be managed by the user via the mobile application 908a and/or which may interface with the user device 908. The measurement devices may include physiological characteristic measurement devices such as the peripheral measurement devices 904, measurement device 110, the wearable device 901, and so forth. The devices module 1004d may include programming which may correlate measurement data received by the user device 908 with a corresponding measurement device. The programming may include assigning an identifying tag to the corresponding measurement device, searching received measurement data for the identifying tag, and/or categorizing the received measurement data with the corresponding measurement device.

The menu module 1004e may include programming which may display to the user a list of the modules associated with the mobile application 908a. The modules may include, the rewards module 1004a, the history module 1004b, the messages module 1004c, the devices module 1004c, a profile module, an appointment module, a share module, a healthcare provider finder module, and so forth. The user may select a module via the menu module 1004e. The menu module 1004e may include programming which may redirect the user in the mobile application 908a to the selected module. In an embodiment, the user may select the profile module in the menu module 1004e. The profile module may be displayed to the user via the GUI 1002b. The user may edit the profile module. The profile module may include demographic and/or identifying information about the user. The profile module may include an identifier which may identify a type of user the user is. For example, the user may be a patient, a healthcare provider, a third party granted access to the patient's health information, and so forth.

It is to be understood that the above description is intended to be illustrative and not restrictive. Many other implementations will be apparent to those of skill in the art upon reading and understanding the above description. The scope of the present implementations should, therefore, be determined with reference to the appended claims, along with the full scope of equivalents to which such claims are entitled.

The disclosure above encompasses multiple distinct embodiments with independent utility. While these embodiments have been disclosed in a particular form, the specific embodiments disclosed and illustrated above are not to be considered in a limiting sense as numerous variations are possible. The subject matter of the embodiments includes the novel and non-obvious combinations and sub-combinations of the various elements, features, functions and/or properties disclosed above and inherent to those skilled in the art pertaining to such embodiments. Where the disclosure or subsequently filed claims recite "a" element, "a first" element, or any such equivalent term, the disclosure or claims is to be understood to incorporate one or more such elements, neither requiring nor excluding two or more such elements.

Applicant(s) reserves the right to submit claims directed to combinations and sub-combinations of the disclosed embodiments that are believed to be novel and non-obvious. Embodiments embodied in other combinations and sub-combinations of features, functions, elements and/or properties may be claimed through amendment of those claims or presentation of new claims in the present application or in a related application. Such amended or new claims, whether they are directed to the same embodiment or a different embodiment and whether they are different, broader, narrower or equal in scope to the original claims, are to be considered within the subject matter of the embodiments described herein.

The invention claimed is:

1. An integrated system, comprising:
   a glucometer comprising:
     a measurement component configured to:
       receive a blood glucose test strip containing a sample of blood of an individual, wherein the blood glucose test strip is received at a first end of the glucometer; and
       determine a blood glucose measurement of the sample of blood; and
     a first port extending from a first end of the glucometer and configured to transmit the blood glucose measurement;
     a first power management component coupled to the first port and configured to manage powering of the glucometer; and
     a first coupler disposed on a second opposite end of the glucometer;

a mobile device communicatively and physically coupled to the glucometer, the mobile device comprising:
  a second port configured to matingly couple with the first port of the glucometer;
  a communication component coupled to the second port and configured to:
    receive the blood glucose measurement from glucometer via the first port and the second port; and
    wirelessly transceive first data over a cellular network;
  a second power management component coupled to the second port and configured to transmit power to the first power management component of the glucometer via the first port and the second port, wherein the mobile device is a power source to the glucometer;
  a third port coupled to the second power management component and configured to receive power from a power source to power the mobile device, wherein the third port is a same type of port as the second port;
  a second coupler matingly and resiliently coupled with the first coupler of the glucometer to releasably maintain coupling of the mobile device with the glucometer;
  a display configured to display the blood glucose measurement; and
a housing configured to house the glucometer and the mobile device, the housing comprising:
  a substantially open cavity, wherein the mobile device is seated in the substantially open cavity and the display of the mobile device is exposed; and
  a substantially closed cavity, wherein the glucometer is substantially enclosed within the substantially closed cavity, wherein the housing wraps around both the mobile device when seated in the substantially open cavity of the housing and the glucometer when enclosed in the substantially closed cavity of the housing, to form a single solitary glucose monitoring system.

2. The integrated system of claim 1, wherein the first port, the second port and the third port are each configured to:
  transceive data; and
  allow power transmission.

3. The integrated system of claim 1, wherein:
  the first data comprises the blood glucose measurement; and
  the second data is calibration data to calibrate the glucometer.

4. The integrated system of claim 1, wherein: the second power management component is further configured to manage powering of the mobile device.

5. The integrated system of claim 1, wherein the communication component is further configured to:
  transmit second data to the glucometer via the first port and the second port; and
  wirelessly transceive third data with another device over a wireless network, wherein the third data comprises the blood glucose measurement.

6. The integrated system of claim 1, wherein the mobile device further comprises a bottom surface facing a top surface of the glucometer, wherein the bottom surface of the mobile device comprises the coupler, the coupler comprising:
  a first coupler;
  a second coupler; and
  the second port disposed between the first coupler and the second coupler.

7. The integrated system of claim 1, wherein the glucometer further comprises a top surface facing a bottom surface of the mobile device, wherein the top surface of the glucometer comprises a resilient coupler comprising:
  a first resilient hook;
  a second resilient hook; and
  the first port disposed between the first resilient hook and the second resilient hook.

8. The integrated system of claim 1, wherein the resilient coupler of the glucometer is a snap-fit coupler that interlocks with the coupler of the mobile device.

9. The integrated system of claim 1, wherein the housing is molded over the glucometer to form the substantially closed cavity around the glucometer.

10. The integrated system of claim 9, wherein glucometer is embedded within the substantially closed cavity and unable to be removed from the substantially closed cavity.

11. The integrated system of claim 1, wherein the housing further comprises a mutual wall between the substantially open cavity and the substantially closed cavity, wherein the mutual wall comprises an aperture, wherein the glucometer is slidably inserted into the substantially closed cavity via the aperture.

12. The integrated system of claim 1, wherein the mobile device comprises a first width from a first lateral side to a second lateral side of the mobile device; and
  the glucometer comprises a second lateral width from a third lateral side to a fourth lateral side of the glucometer, wherein the first lateral width is equal to the second lateral width.

13. The integrated system of claim 1, wherein:
the first coupler comprises:
  a first resilient flange protruding from the second opposite end; and
  a second resilient flange protruding from the second opposite end; and
the second coupler comprises:
  a third flange configured to matingly and resiliently couple with the first resilient flange;
  a fourth flange configured to matingly and resiliently couple with the second resilient flange.

14. An apparatus comprising:
a glucometer comprising:
  a test strip aperture disposed at a first end of the glucometer and configured to receive a glucose test strip having a sample of blood of an individual;
  a measurement component configured to determine a blood glucose measurement of the sample of blood; and
  a first port disposed at an opposite second of the glucometer and configured to:
    transmit the blood glucose measurement to a mobile device; and
    receive data from the mobile device;
  a power management component coupled to the first port and configured to receive power from the mobile device; and
a housing comprising:
  a first group of surfaces defining a cavity, wherein the glucometer is fully enclosed within the cavity, the first group of surfaces comprising:
    a first surface comprising a first aperture aligned with the test strip aperture of the glucometer; and
    a second surface opposite the first surface, the second surface comprising a second aperture aligned with the first port of the glucometer; and a second group of surfaces defining an open cavity configured to house the mobile device, wherein the second group of surfaces comprise the second surface of the first group of surfaces.

15. The apparatus of claim 14, wherein the first port is a Universal Serial Bus (USB) Type-C plug configured to extend through the second aperture.

16. The apparatus of claim 14, wherein the glucometer further comprises a resilient coupler configured to resiliently couple with the mobile device, wherein the resilient coupler extends through the second aperture.

17. The apparatus of claim 14, further comprising a mobile device communicatively and physically coupled to the glucometer.

18. A hand-held device comprising:
- a mobile device configured to communicatively and physically couple to a glucometer, the mobile device comprising:
  - a first port disposed on a first exterior wall of the mobile device and configured to:
    - matingly couple with a port of the glucometer;
    - receive blood glucose measurements of an individual from the glucometer; and
    - receive a power source to power the mobile device when the glucometer is not matingly coupled to the mobile device at the first port;
  - a second port disposed on a second exterior wall of the mobile device, wherein the first port is a first type and the second port is a second type, and the second port is configured to:
    - receive the power source to power the mobile device or charge a battery when the glucometer is matingly coupled to the mobile device at the first port; and
  - a power management component coupled to the first port and the second port and configured to:
    - manage powering of the mobile device; and
    - transmit power to the glucometer via the first port, wherein the mobile device is a power source to the glucometer; and
- a housing comprising:
  - a first cavity, wherein the mobile device is disposed in the first cavity; and
  - a second cavity configured to enclose the glucometer, wherein the housing wraps around both the mobile device when disposed in the first cavity of the housing and the glucometer when enclosed in the second cavity of the housing, to form a single solitary glucose monitoring system.

19. The hand-held device of claim 18, wherein the housing further comprises a speaker aperture aligned with a respective speaker of the mobile device, wherein the speaker aperture is configured to allow sound to emanate from the speaker of the mobile device beyond the housing.

20. The hand-held device of claim 18, wherein the power management component comprises:
- a first power management system configured to manage powering of the mobile device; and
- a second power management system configured to transmit the power to the glucometer.

* * * * *